US012758235B2

(12) United States Patent
Gazonnet et al.

(10) Patent No.: US 12,758,235 B2
(45) Date of Patent: Oct. 13, 2026

(54) REUSABLE SURGICAL GUIDE FOR OSTEOSYNTHESIS SURGERY IN PARTICULAR OF THE HALLUX VALGUS AND METHOD OF USING THE SAME

(71) Applicant: NOVASTEP, Rennes (FR)

(72) Inventors: Lilian Gazonnet, Montrevel en Bresse (FR); Adrien Bousquet, La Meziere (FR); Loïc Girod, Goven (FR); Brian Schauer, Huntersville, NC (US); Brian Loder, Clinton Township, MI (US); Tristan Meusnier, Saint Etienne (FR); Peter Lam, Sydney (AU); Oliver Schipper, Arlington, VA (US); Holly Johnson, Wayland, MA (US)

(73) Assignee: NOVASTEP, Rennes (FR)

( * ) Notice: Subject to any disclaimer, the term of this patent is extended or adjusted under 35 U.S.C. 154(b) by 293 days.

(21) Appl. No.: 18/025,309

(22) PCT Filed: Dec. 17, 2021

(86) PCT No.: PCT/EP2021/086470
§ 371 (c)(1),
(2) Date: Mar. 8, 2023

(87) PCT Pub. No.: WO2022/129511
PCT Pub. Date: Jun. 23, 2022

(65) Prior Publication Data

US 2024/0285291 A1 Aug. 29, 2024

Related U.S. Application Data

(63) Continuation-in-part of application No. 17/126,608, filed on Dec. 18, 2020, now Pat. No. 12,133,655.
(Continued)

(30) Foreign Application Priority Data

Dec. 18, 2020 (FR) ..................................... 20/13711
Sep. 20, 2021 (FR) ..................................... 21/09855

(51) Int. Cl.
*A61B 17/17* (2006.01)
*A61B 17/16* (2006.01)
(Continued)

(52) U.S. Cl.
CPC ...... *A61B 17/1739* (2013.01); *A61B 17/1697* (2013.01); *A61B 17/8861* (2013.01); *A61B 2017/00367* (2013.01); *A61B 17/90* (2021.08)

(58) Field of Classification Search
CPC . A61B 17/1697; A61B 17/90; A61B 17/8861; A61B 17/1775; A61B 17/1782;
(Continued)

(56) References Cited

U.S. PATENT DOCUMENTS 4,672,957 A 6/1987 Hourahane
5,891,150 A * 4/1999 Chan .................. A61B 17/1714 606/98

(Continued)

FOREIGN PATENT DOCUMENTS

CN 114848086 A 8/2022
CN 115192160 A 10/2022

(Continued)

OTHER PUBLICATIONS

Mar. 14, 2022 International Search Report issued in International Patent Application No. PCT/EP2021/086470.

(Continued)

*Primary Examiner* — Amy R Sipp
(74) *Attorney, Agent, or Firm* — Eversheds Sutherland (US) LLP

(57) ABSTRACT

A reusable surgical guide for osteosynthesis surgery, for the insertion of wires into bone portions, and a method of using
(Continued)

the same. The guide includes a grip including a head extending an end of a base, a blade secured to the head, a trigger that is displaceable in a first slide formed in the head, and an aiming piece that is displaceable in a second slide formed in the base. The trigger includes a guide element for insertion of a pull wire, and the aiming piece includes a means for supporting at least one positioning wire. The method includes retracting the trigger to move a first bone portion relative to a second bone portion; and inserting a first wire through the supporting means and into the first and second bone portions in a state in which the surgical guide and a draw wire holds relative positions of the bone portions.

11 Claims, 36 Drawing Sheets

Related U.S. Application Data

(60) Provisional application No. 63/246,102, filed on Sep. 20, 2021.

(51) Int. Cl.
*A61B 17/88* (2006.01)
*A61B 17/00* (2006.01)
*A61B 17/90* (2006.01)

(58) Field of Classification Search
CPC ............ A61B 17/1739; A61B 17/1721; A61B 17/1725; A61B 17/1717; A61B 17/1714; A61B 17/1764
See application file for complete search history.

(56) References Cited

U.S. PATENT DOCUMENTS 6,860,883 B2 * 3/2005 Janowski ............ A61B 17/645 606/56
8,617,176 B2 12/2013 Lizardi et al.
8,663,233 B2 3/2014 Suda
8,821,504 B2 9/2014 Sharkey et al.
9,498,370 B2 11/2016 Taylor et al.
10,524,808 B1 1/2020 Hissong et al.
10,610,241 B2 4/2020 Wagner et al.
11,931,088 B2 3/2024 Pyle et al.
12,133,655 B2 11/2024 Gazonnet et al.
12,185,958 B2 1/2025 Korman et al.
12,186,001 B2 1/2025 Korman
12,256,969 B2 3/2025 Korman et al.
2002/0133165 A1 9/2002 Whittaker et al.
2004/0087953 A1 5/2004 Singhatat et al.
2009/0036931 A1 2/2009 Pech et al.
2012/0109136 A1 * 5/2012 Bourque ............ A61B 17/1714 606/87
2015/0157337 A1 6/2015 Wolf et al.
2020/0060698 A1 2/2020 Woodard et al.
2021/0113223 A1 4/2021 Schaumann et al.
2022/0039810 A1 2/2022 Gil et al.
2022/0192685 A1 6/2022 Gazonnet et al.
2023/0052337 A1 2/2023 Carlo, III et al.
2023/0077222 A1 3/2023 Awtrey
2023/0310013 A1 10/2023 Perler et al.
2024/0285291 A1 8/2024 Gazonnet et al.

FOREIGN PATENT DOCUMENTS

CN 115349934 A 11/2022
CN 115486925 A 12/2022
CN 218186919 U 1/2023
CN 218305077 U 1/2023
CN 219578952 U 8/2023
CN 117297711 A 12/2023
CN 117838278 A 4/2024
CN 221205617 U 6/2024
CN 118319456 A 7/2024
CN 118453027 A 8/2024
CN 221533971 U 8/2024
CN 118662213 A 9/2024
EP 2561815 A1 2/2013
EP 3 583 905 A1 12/2019
FR 2911264 A1 7/2008
JP H11267135 A 10/1999
JP 2013043093 A 3/2013
KR 102604463 B1 11/2023
WO 0025681 A1 5/2000
WO 2013/123366 A1 8/2013
WO 2014013517 A1 1/2014
WO 2017/040843 A1 3/2017
WO 2018/183875 A1 10/2018
WO 2019246332 A1 12/2019
WO 2020/041841 A1 3/2020
WO 2025/059089 A1 3/2025
WO 2025064674 A1 3/2025

OTHER PUBLICATIONS

Mar. 14, 2022 Written Opinion of the International Searching Authority issued in International Patent Application No. PCT/EP2021/086470.
Apr. 23, 2024 Office Action issued in U.S. Appl. No. 17/126,608.
Mcmater-Carr, "Metal Worms and Worm Gears", Https://www.mcmaster.com/worm-screws/, accessed Mar. 14, 2023 (Year: 2023).
Mar. 17, 2023 Office Action Issued In U.S. Appl. No. 17/126,608.
U.S. Appl. No. 17/126,608, filed Dec. 18, 2020 in the name of Lilian Gazonnet et al.
Oct. 10, 2023 Office Action issued in U.S. Appl. No. 17/126,608.
International Search Report and the Written Opinion of the International Application No. PCT/US2019/038116 dated Sep. 20, 2019 (14 pages).
International Preliminary Report on Patentability for International Application No. PCT/US2019/038116 dated Dec. 30, 2020 (9 pages).

* cited by examiner

[Fig. 1]
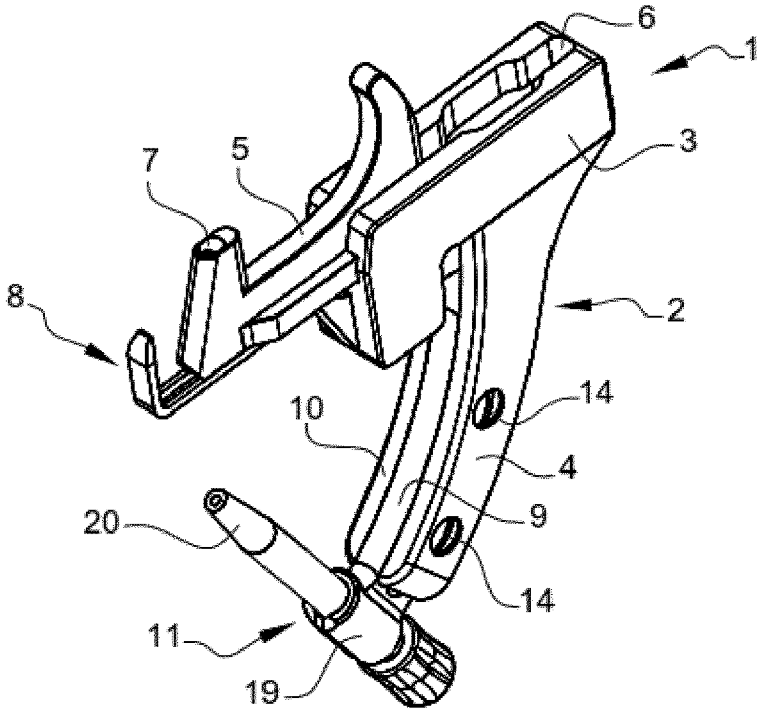
[Fig. 2]
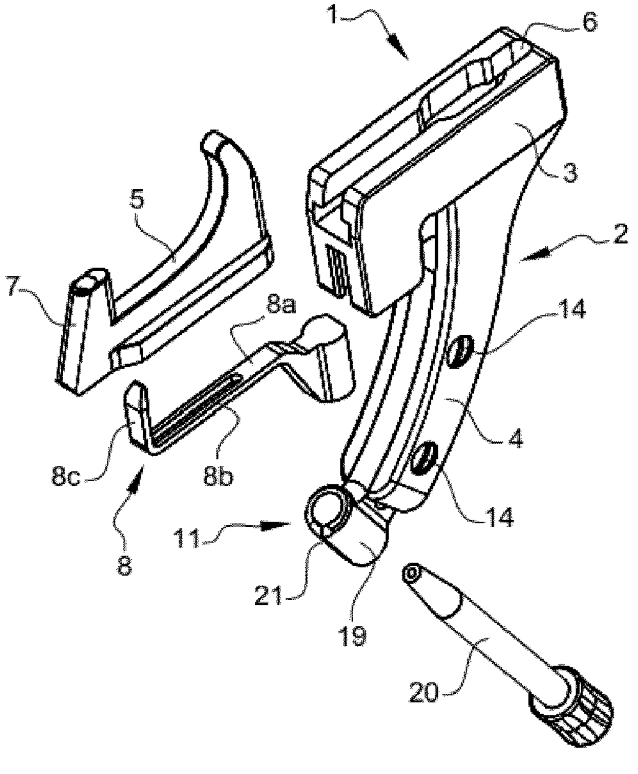

[Fig. 3]
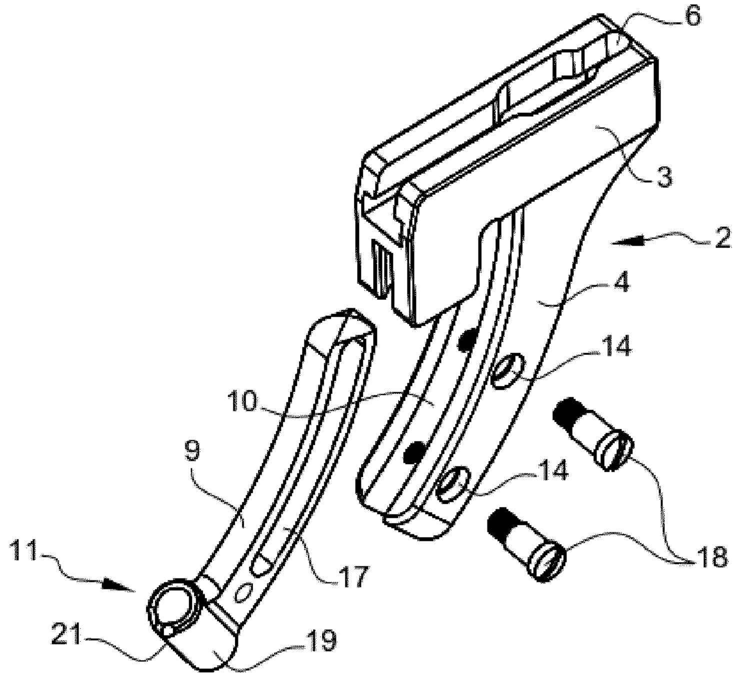
[Fig. 4]
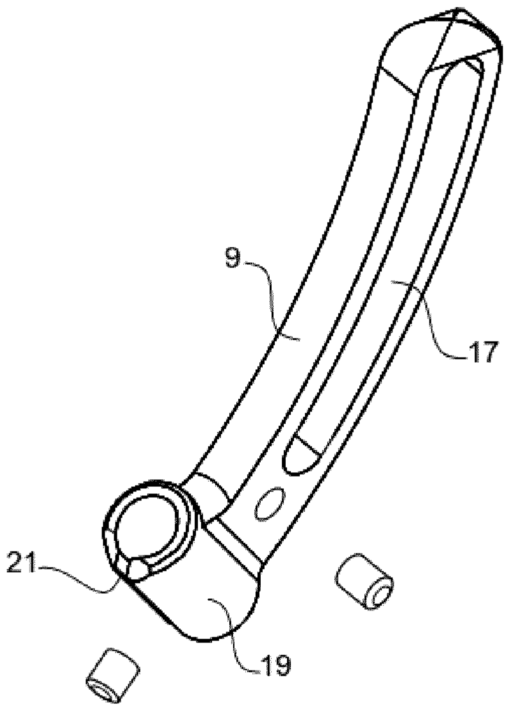

[Fig. 5]
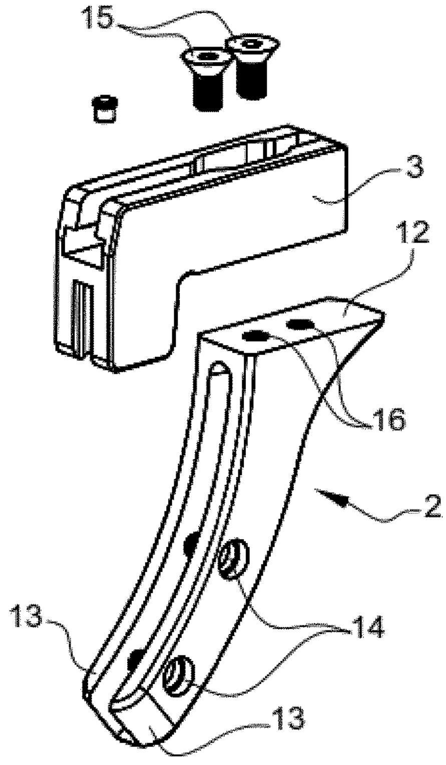
[Fig. 6]
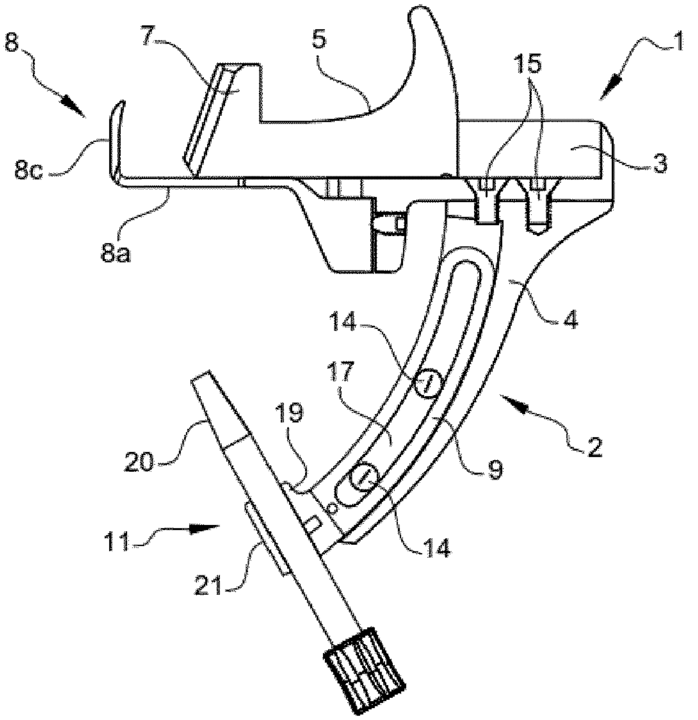

[Fig. 7]
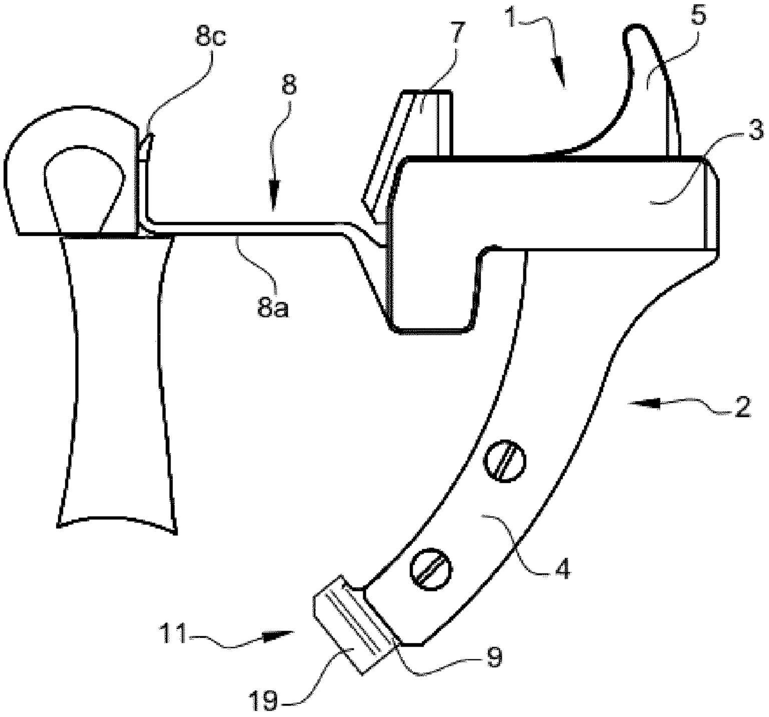
[Fig. 8]
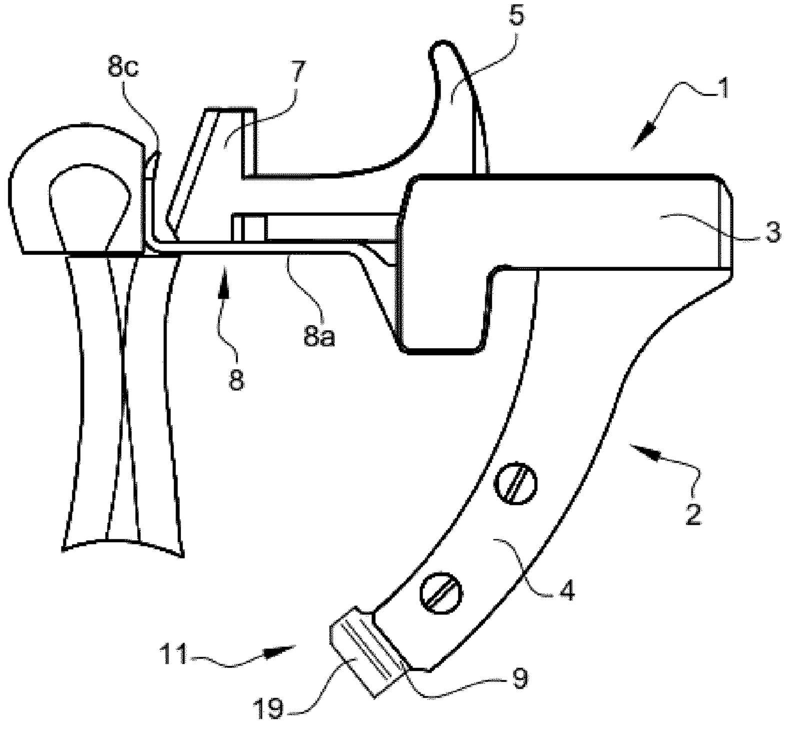

[Fig. 9]
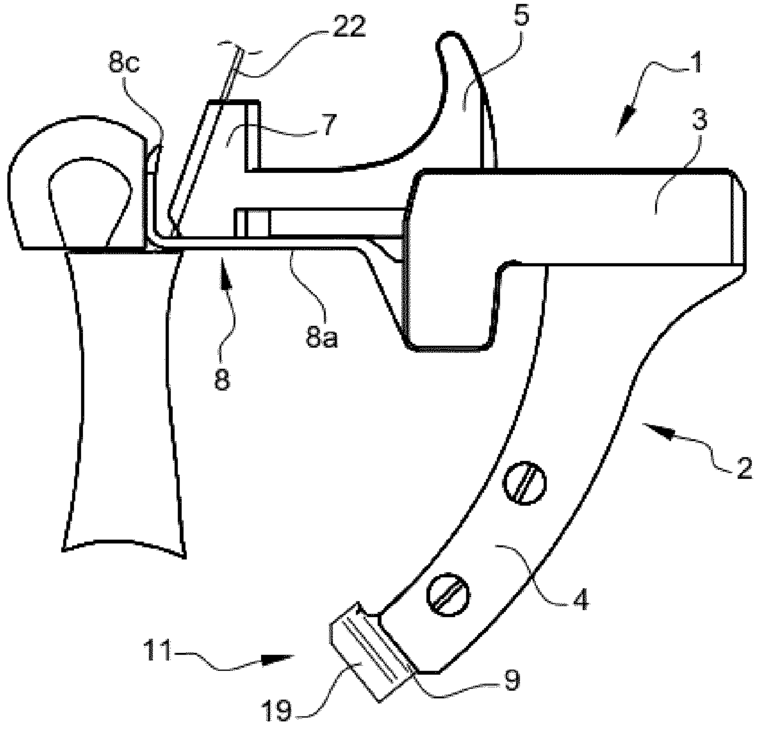
[Fig. 10]
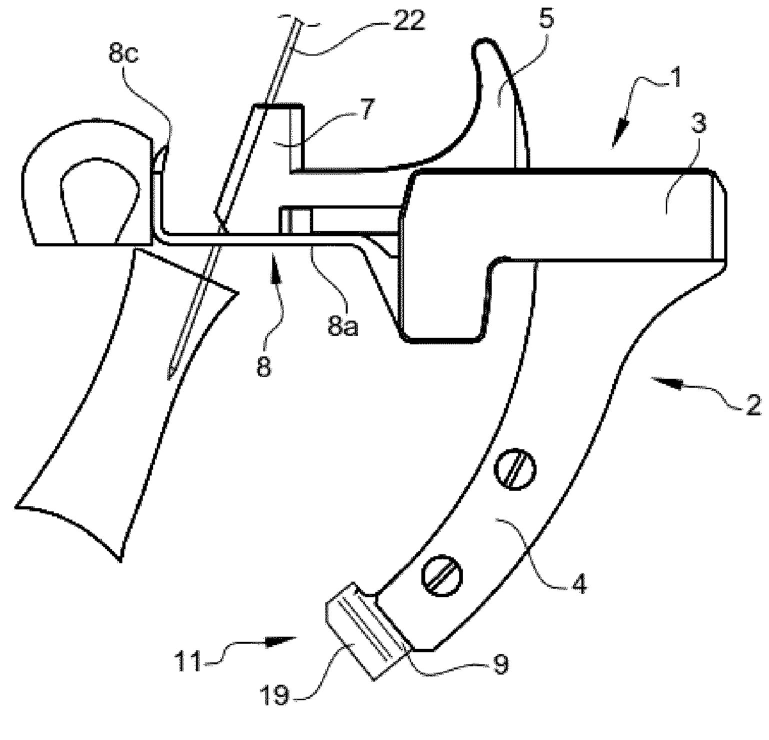

[Fig. 11]
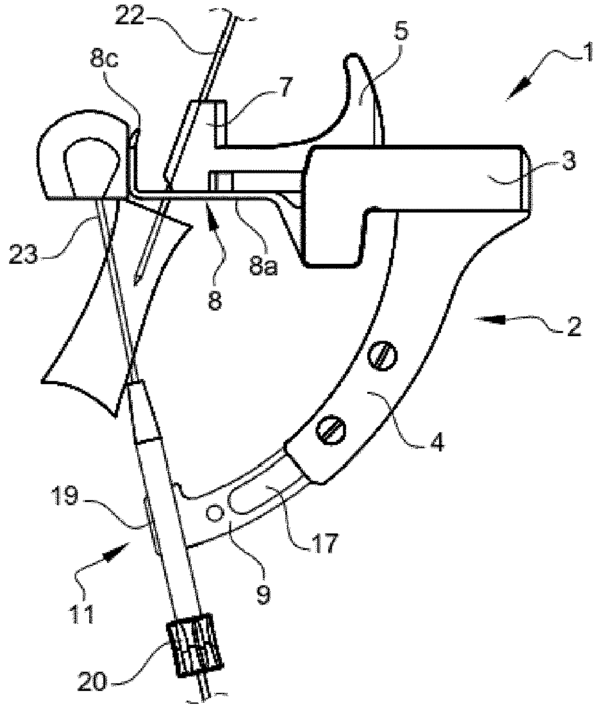
[Fig. 12]
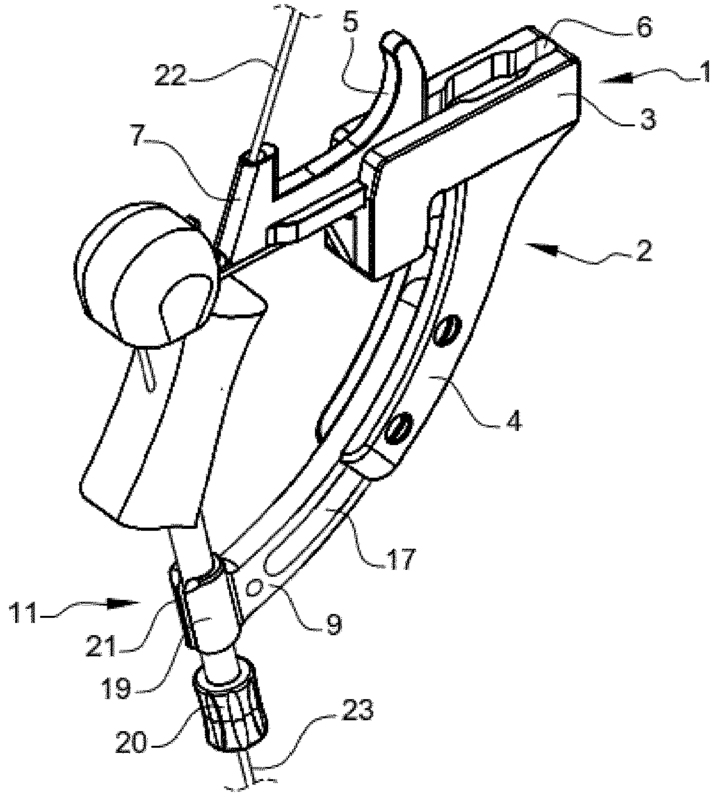

[Fig. 13]
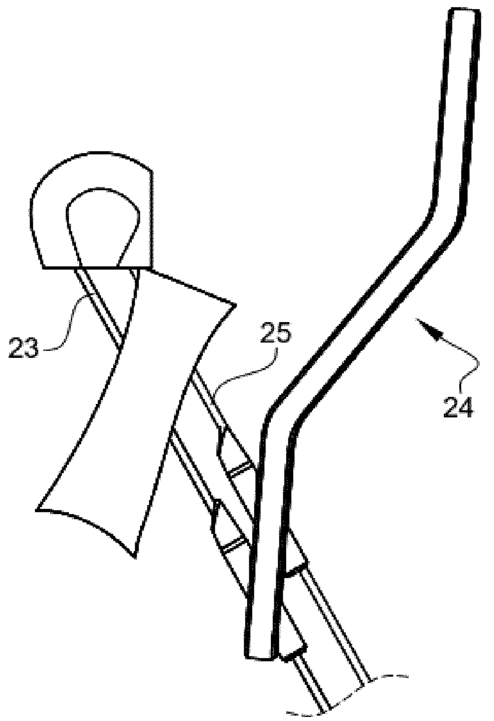
[Fig. 14]
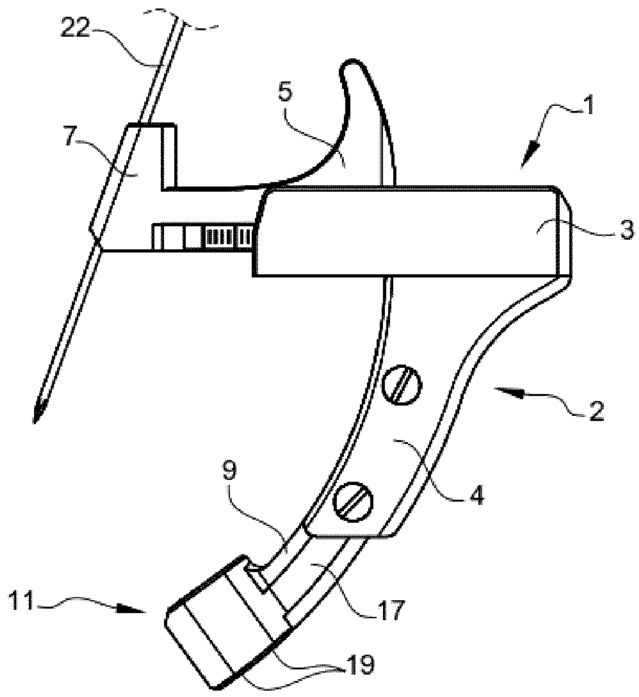

[Fig. 15]
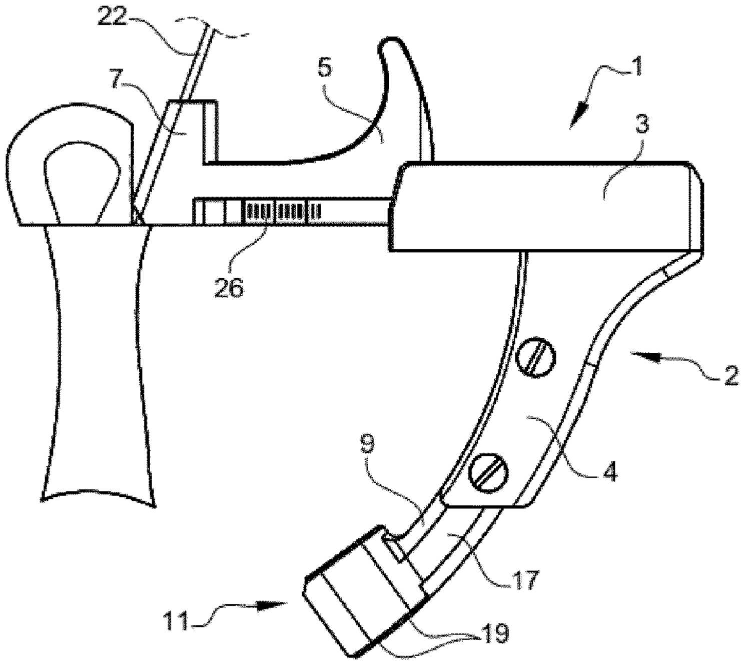
[Fig. 16]
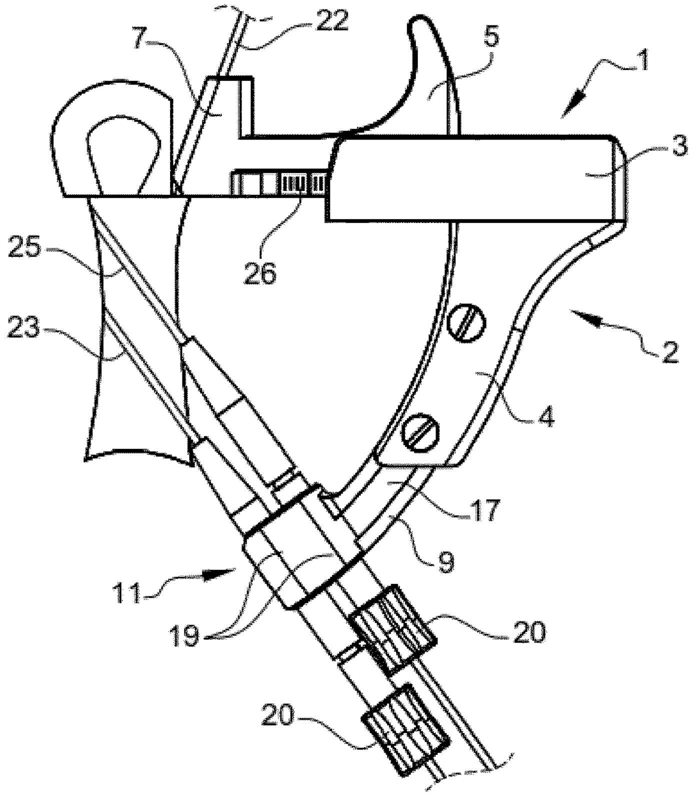

[Fig. 17]
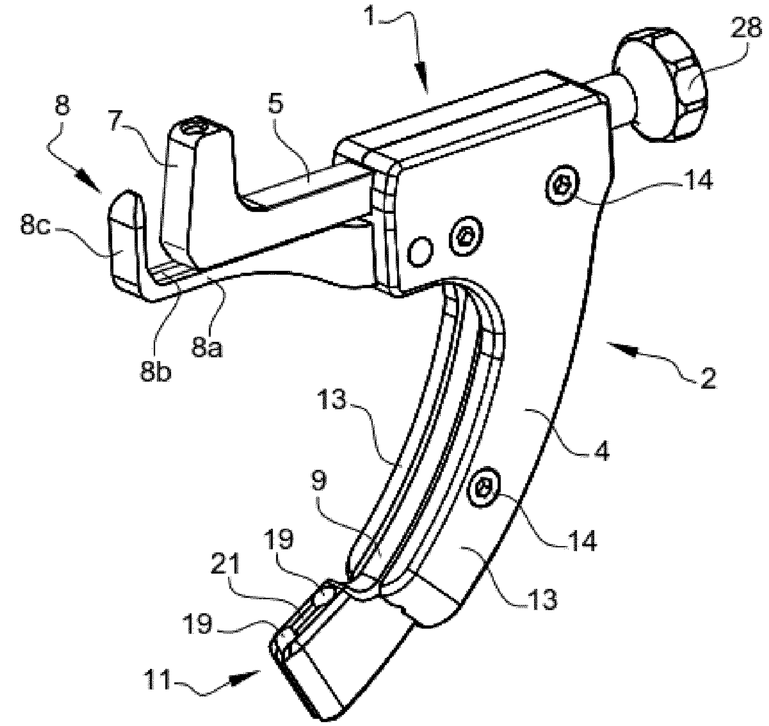
[Fig. 18]
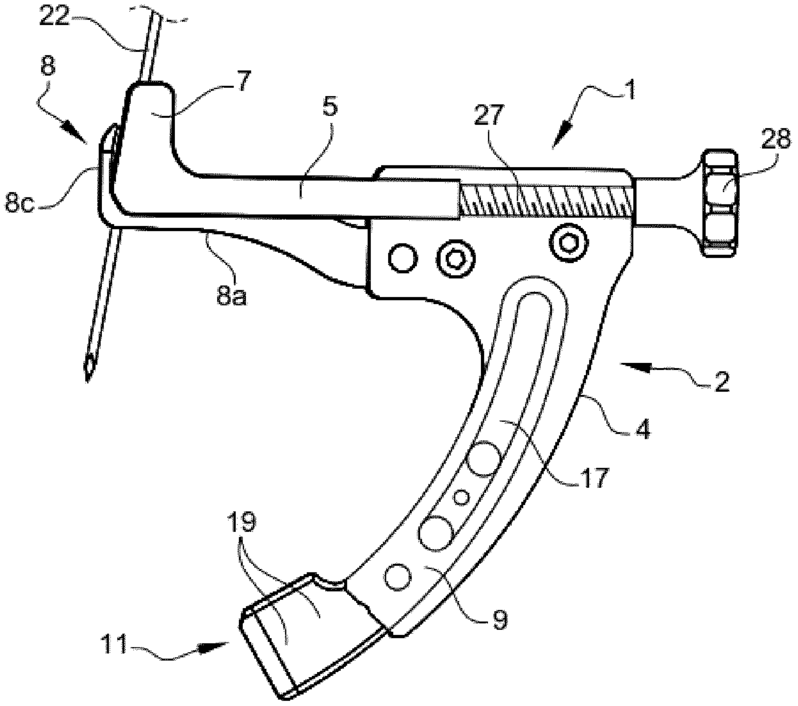

[Fig. 19]
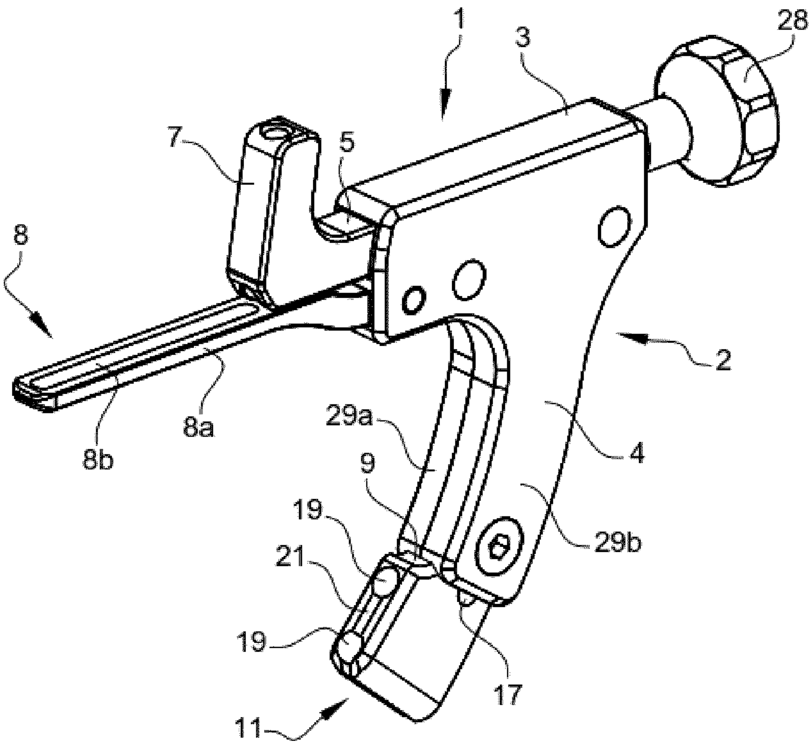
[Fig. 20]
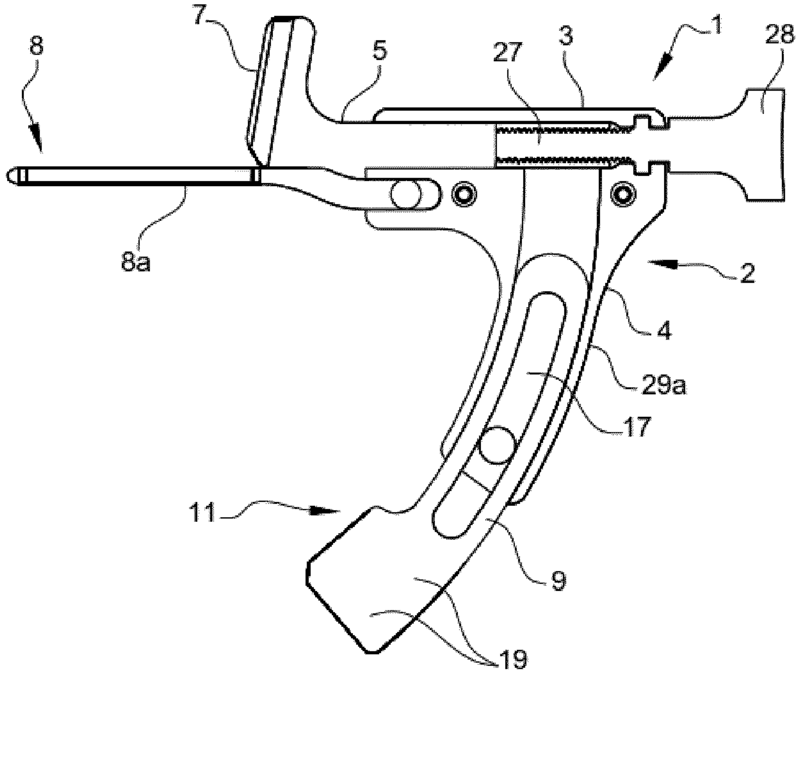

[Fig. 21]
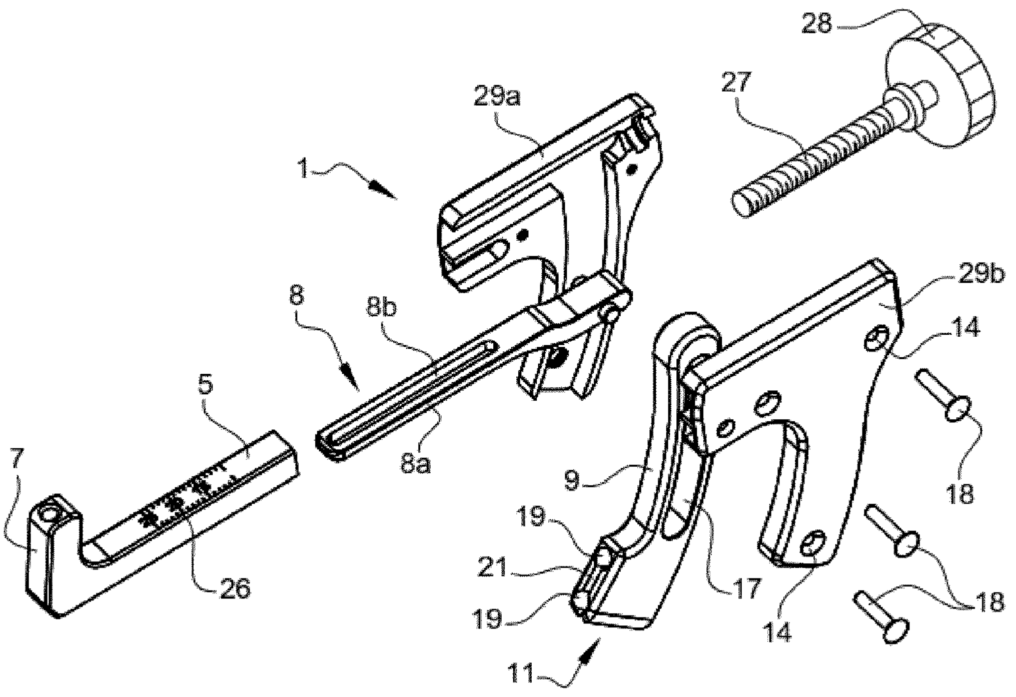
[Fig. 22]
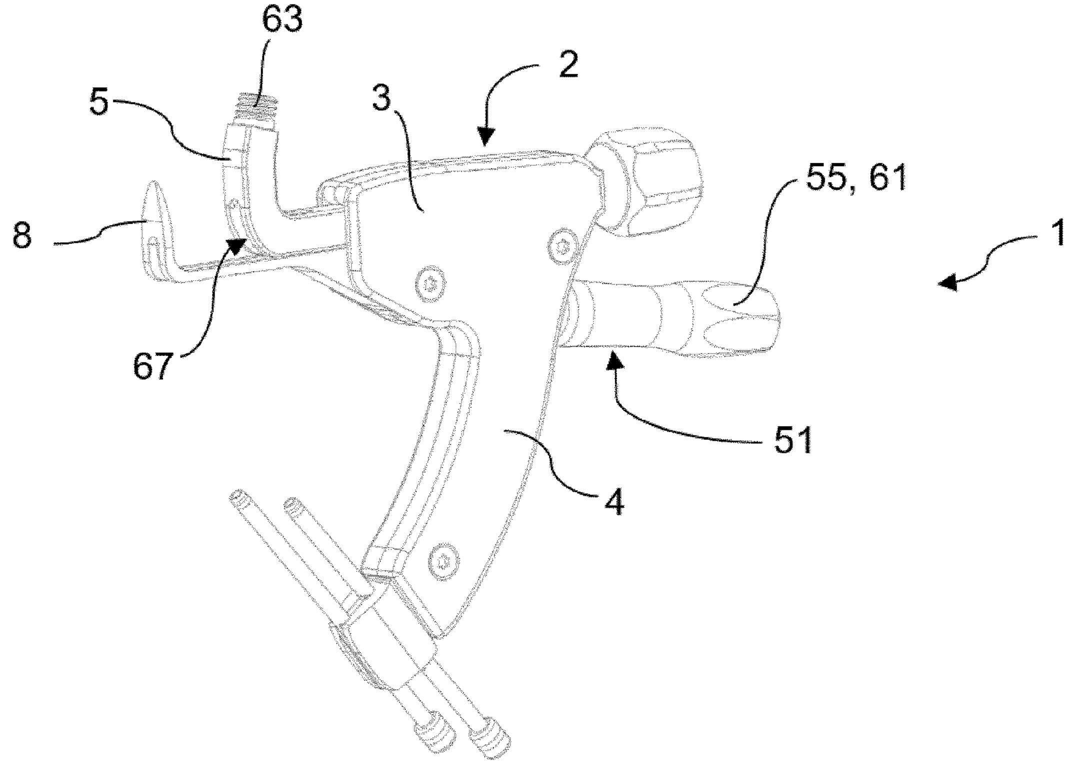

[Fig. 23]
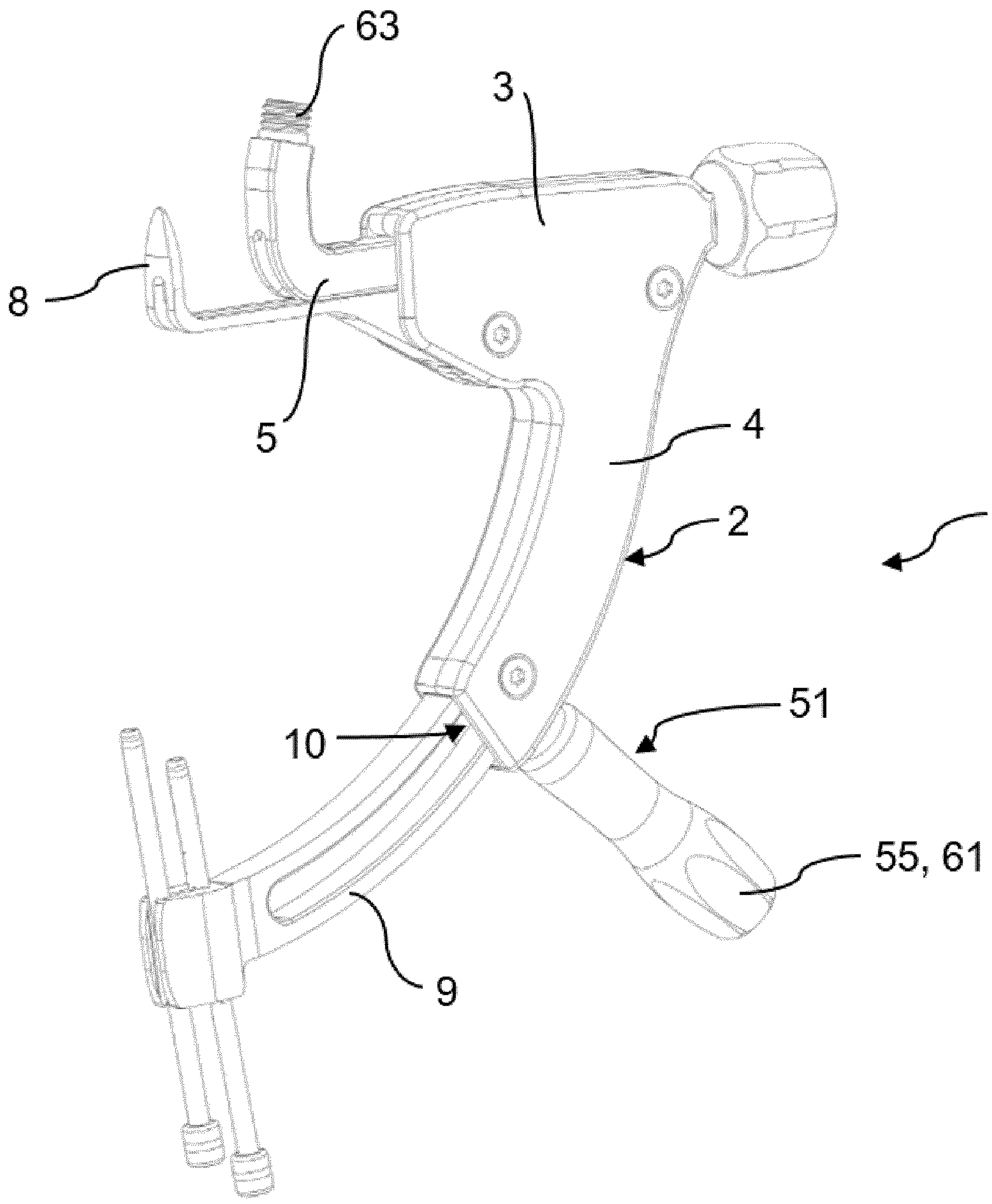

[Fig. 24]
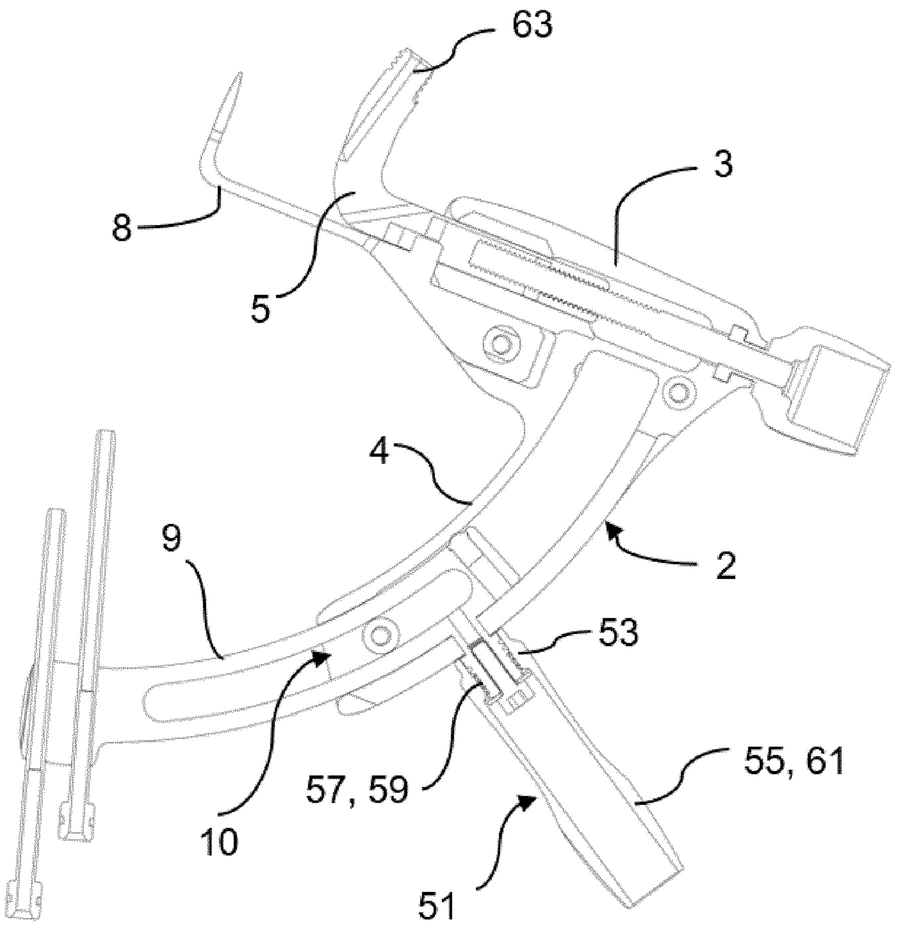

[Fig. 25]
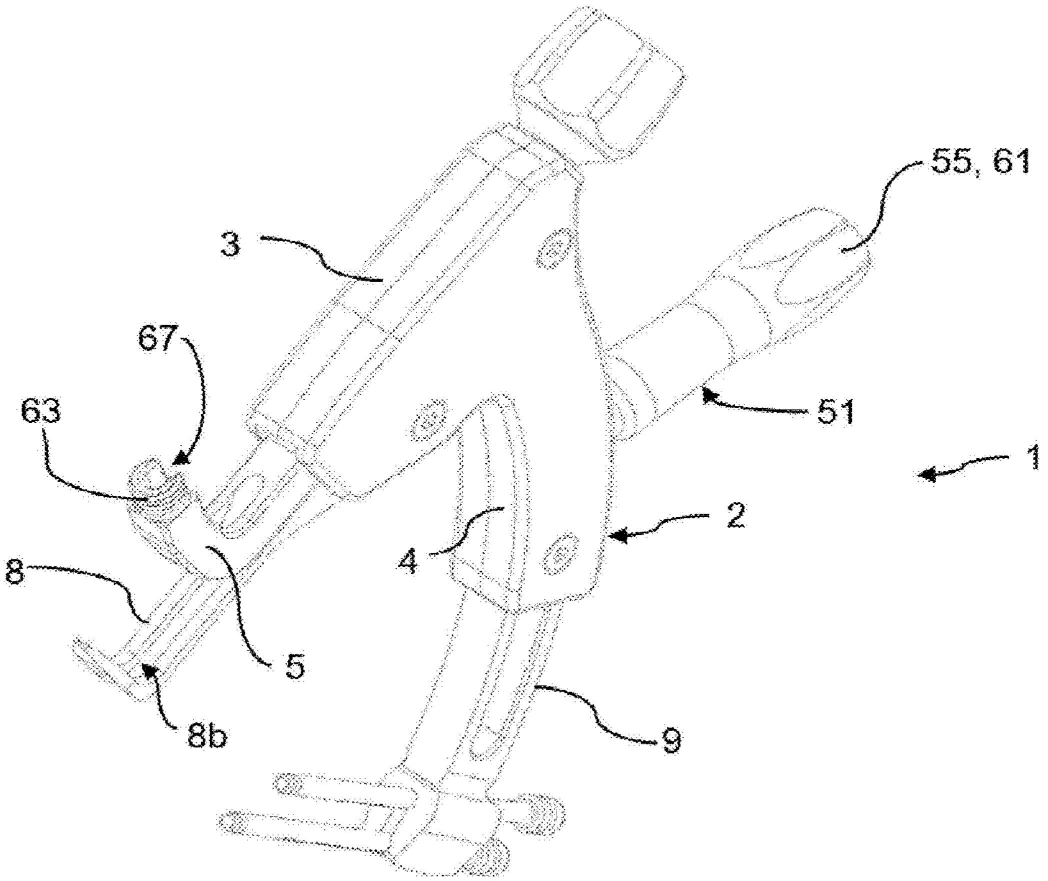

[Fig. 26]
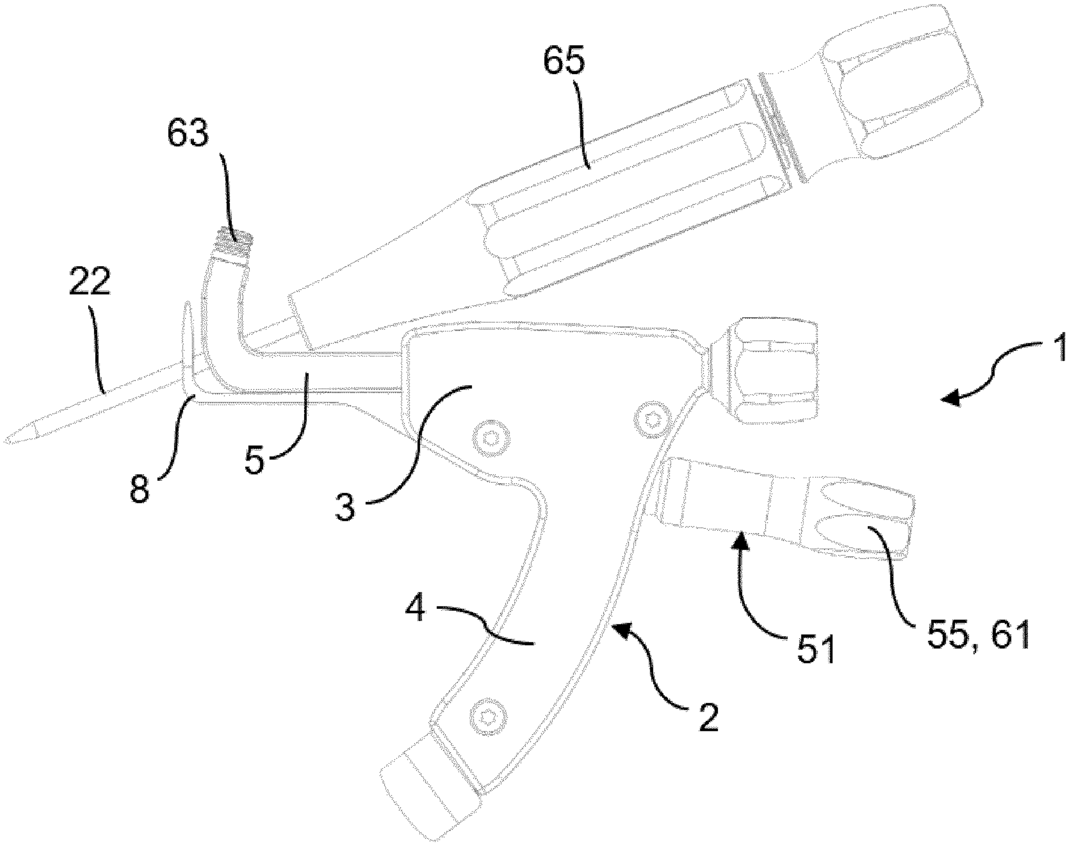

[Fig. 27]
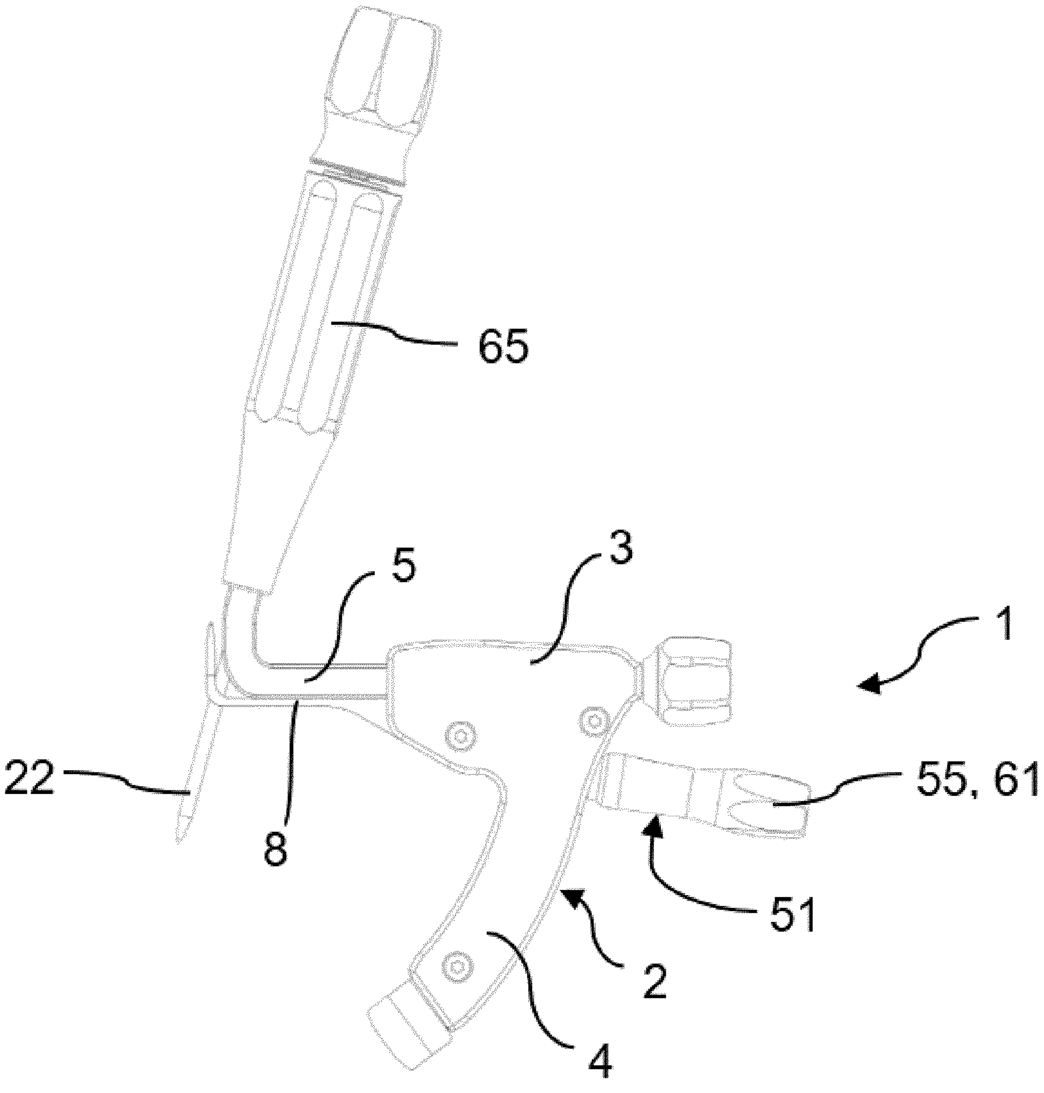

[Fig. 28A]
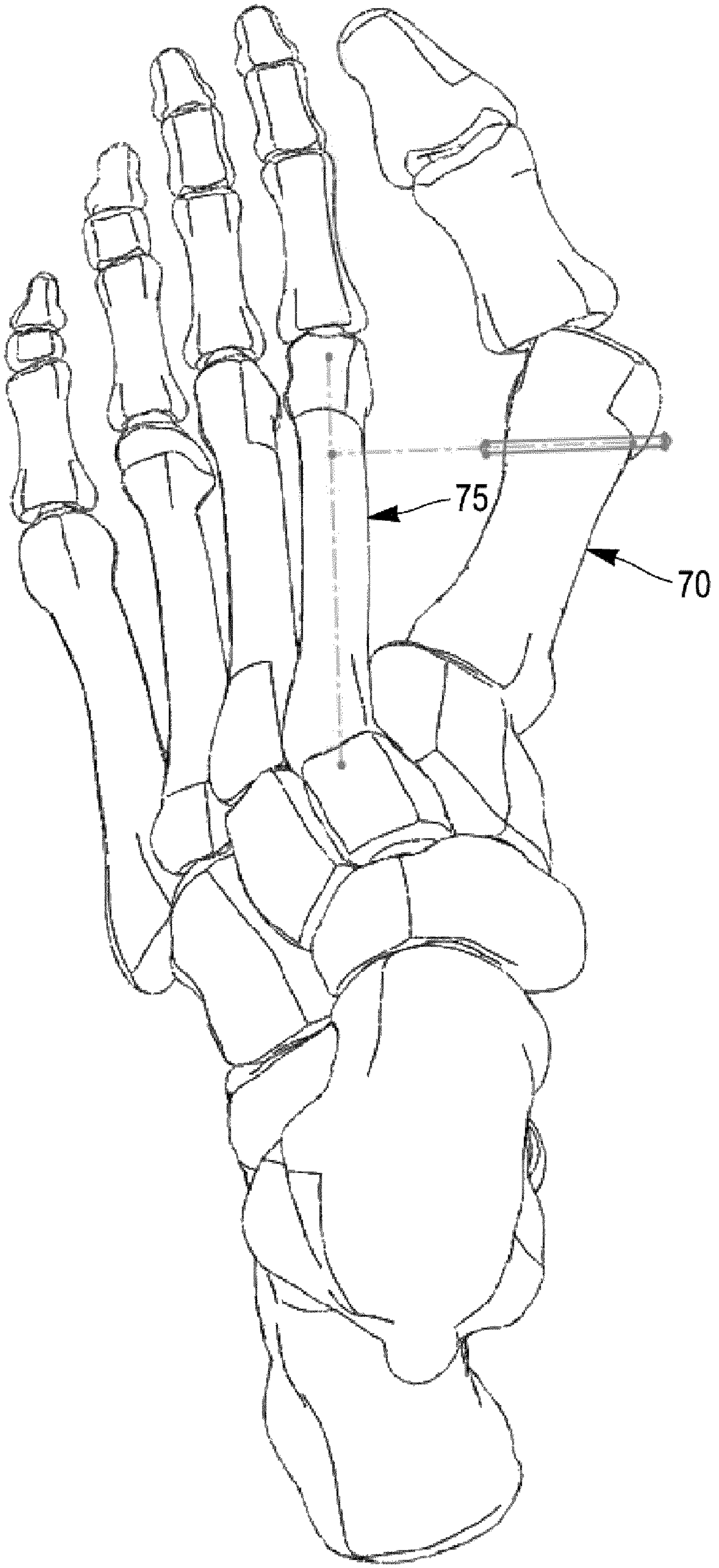

[Fig. 28B]
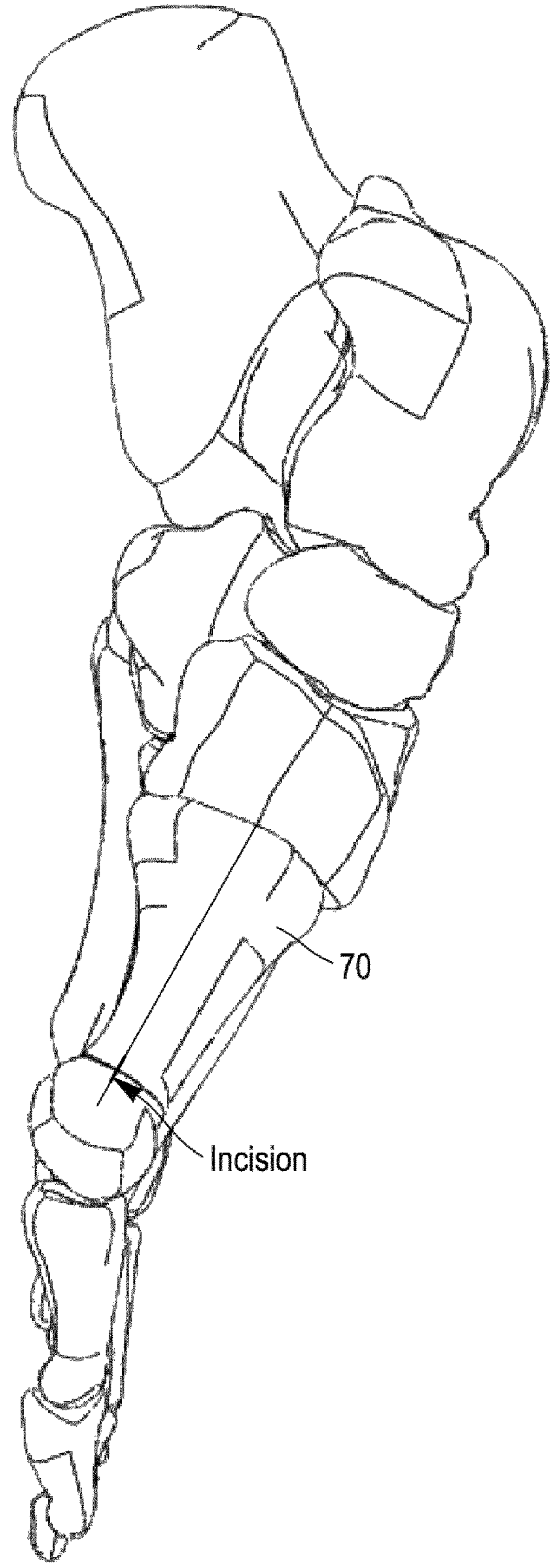

[Fig. 29A]
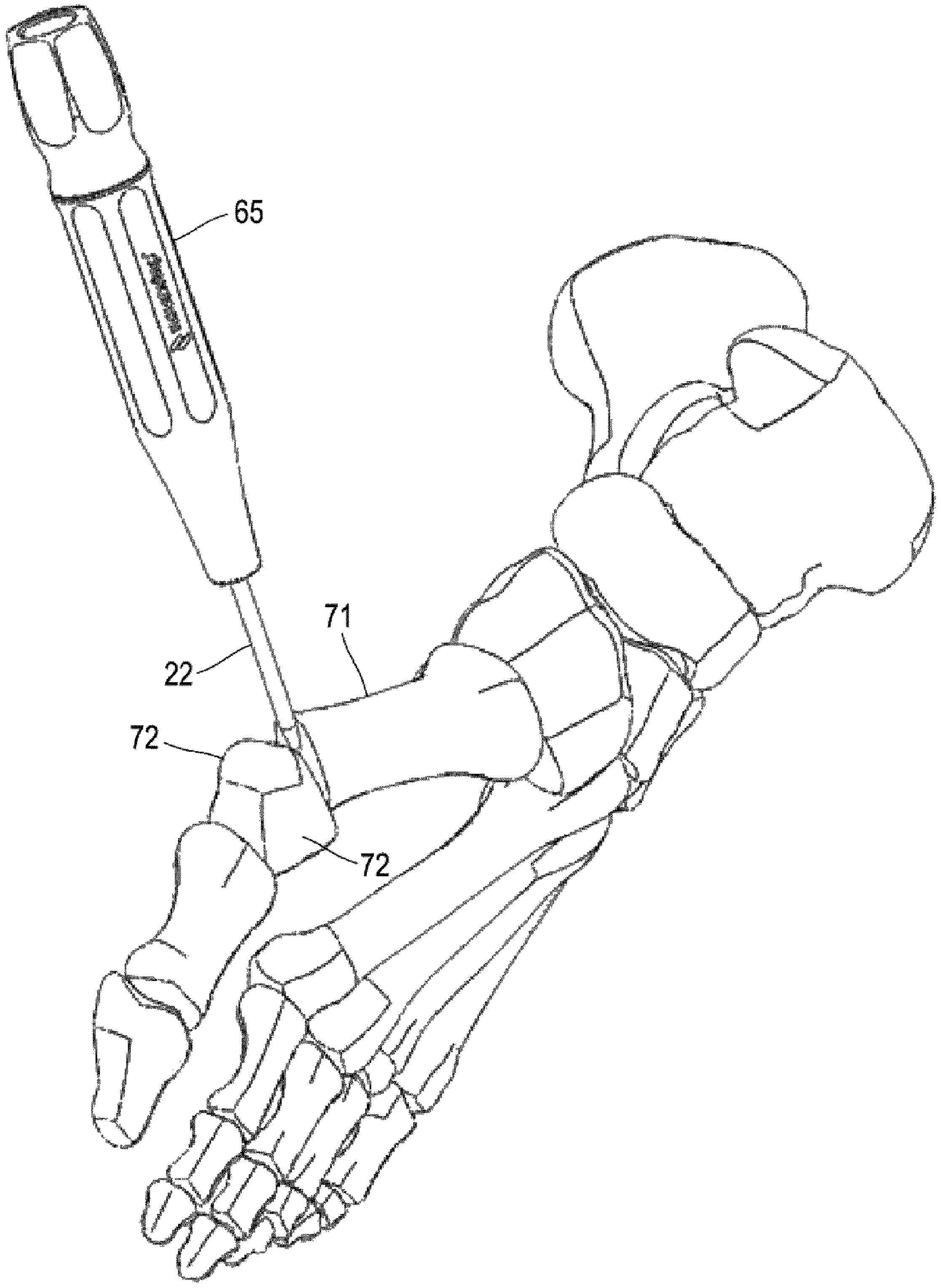

[Fig. 29B]
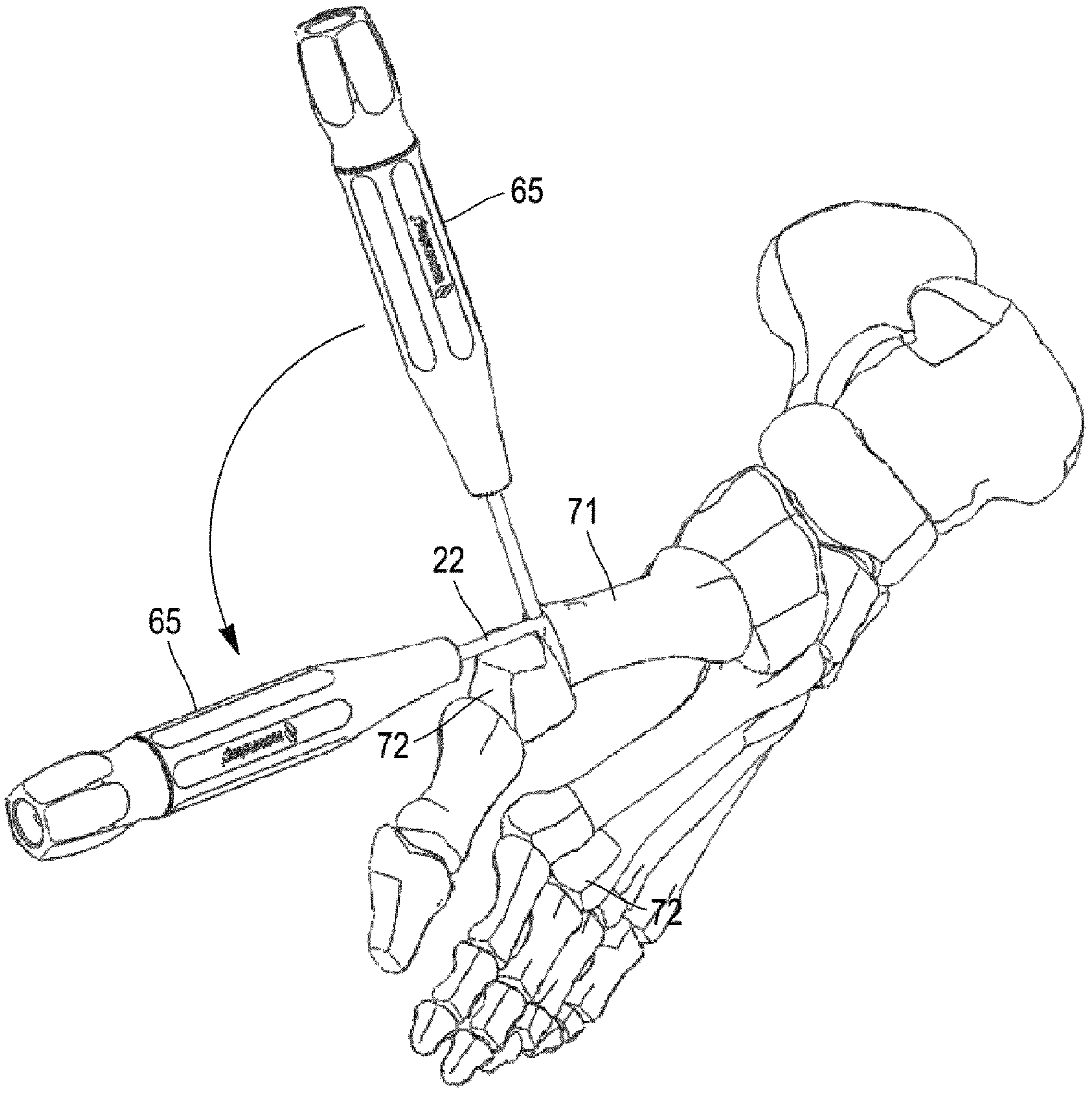

[Fig. 29C]
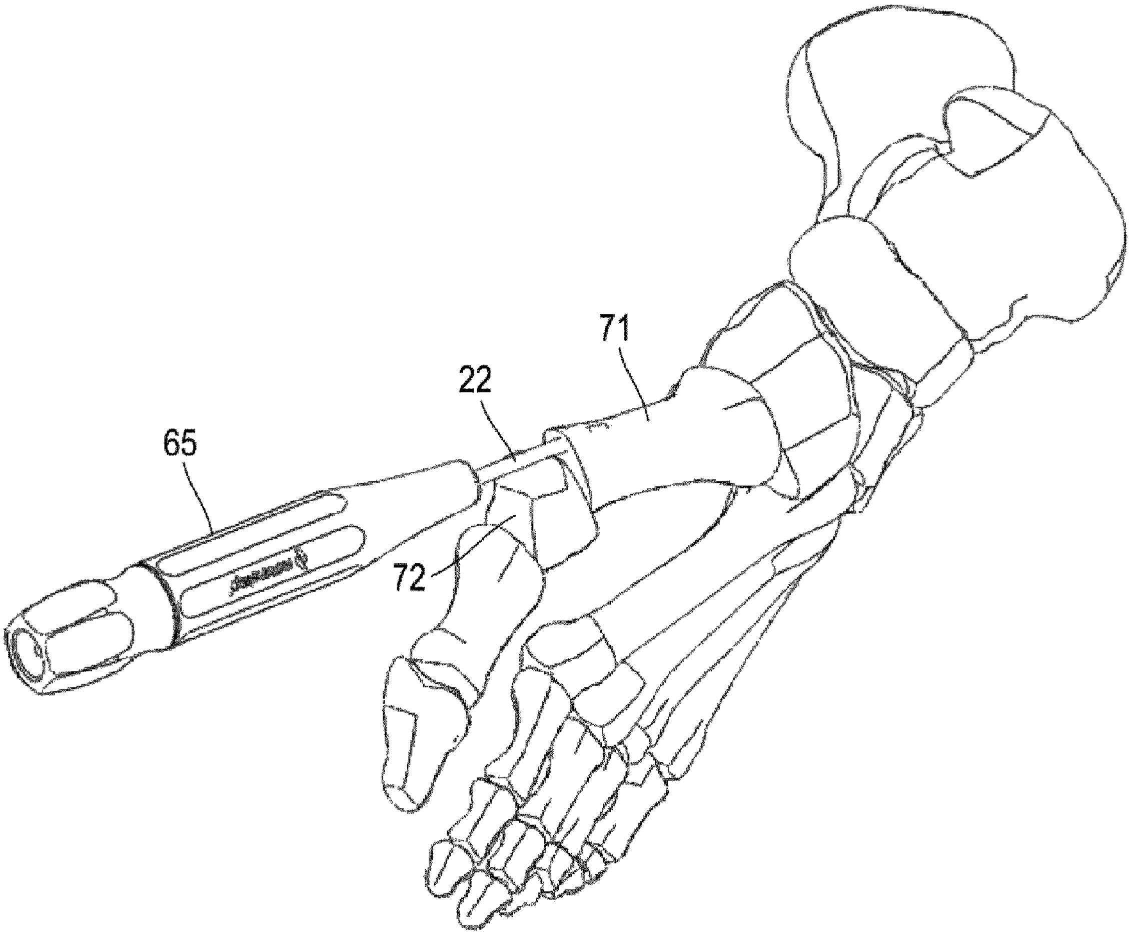

[Fig. 30A]
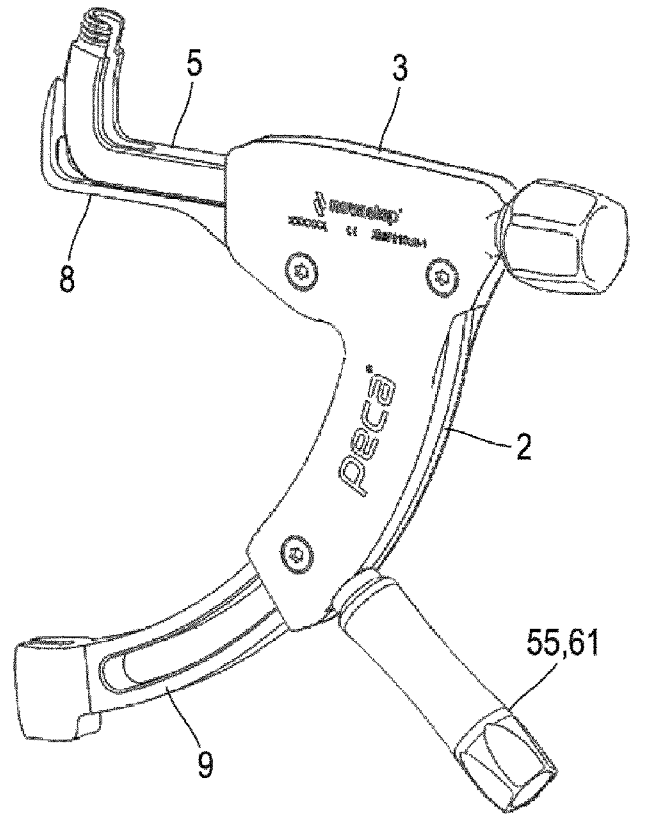
[Fig. 30B]
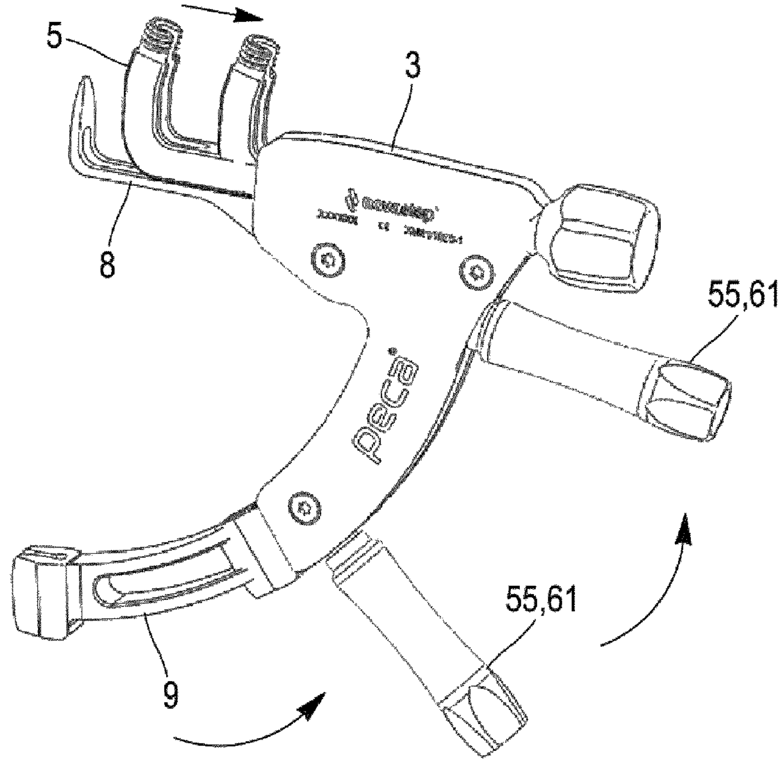

[Fig. 30C]
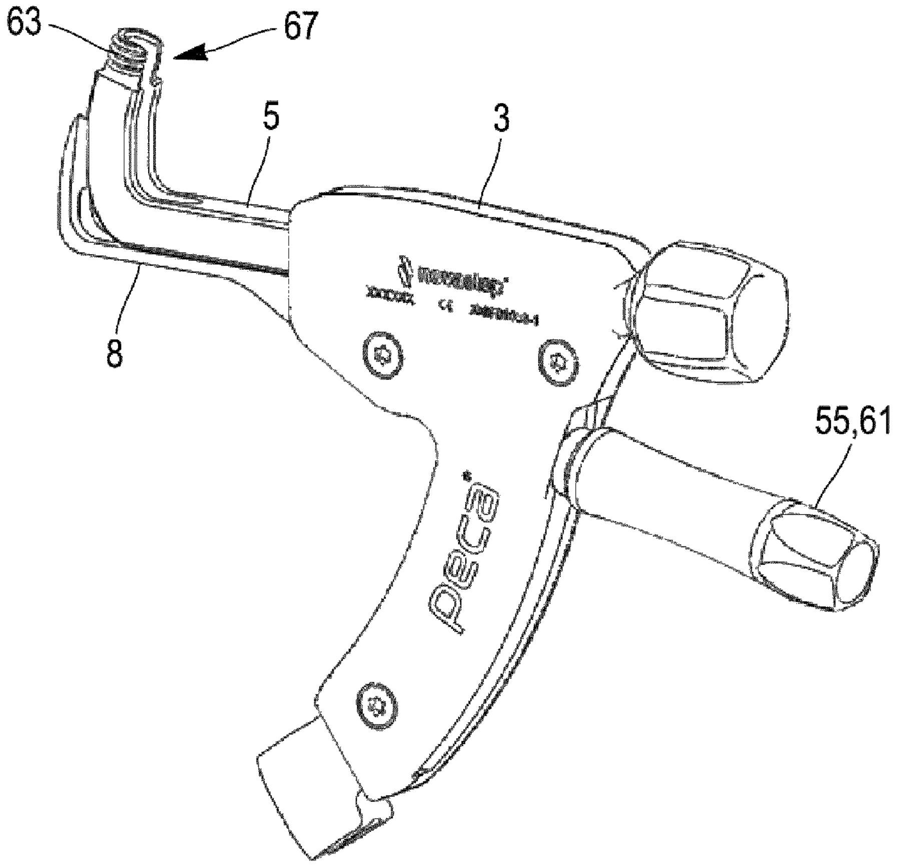

[Fig. 30D]
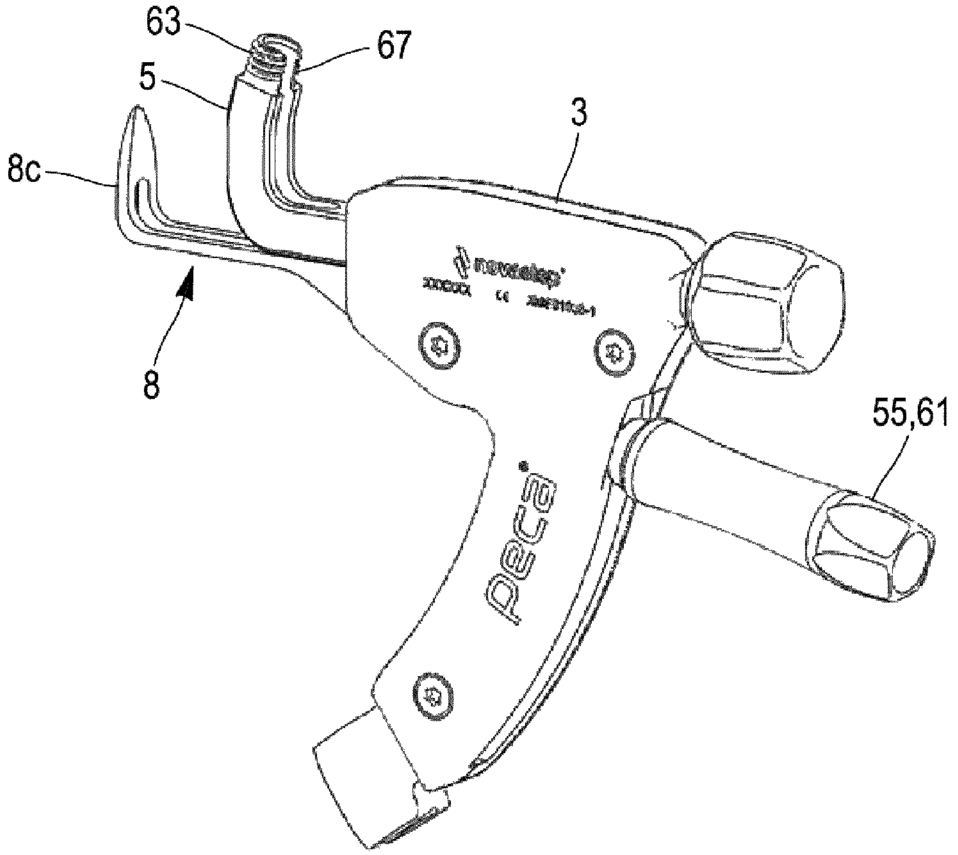

[Fig. 31A]
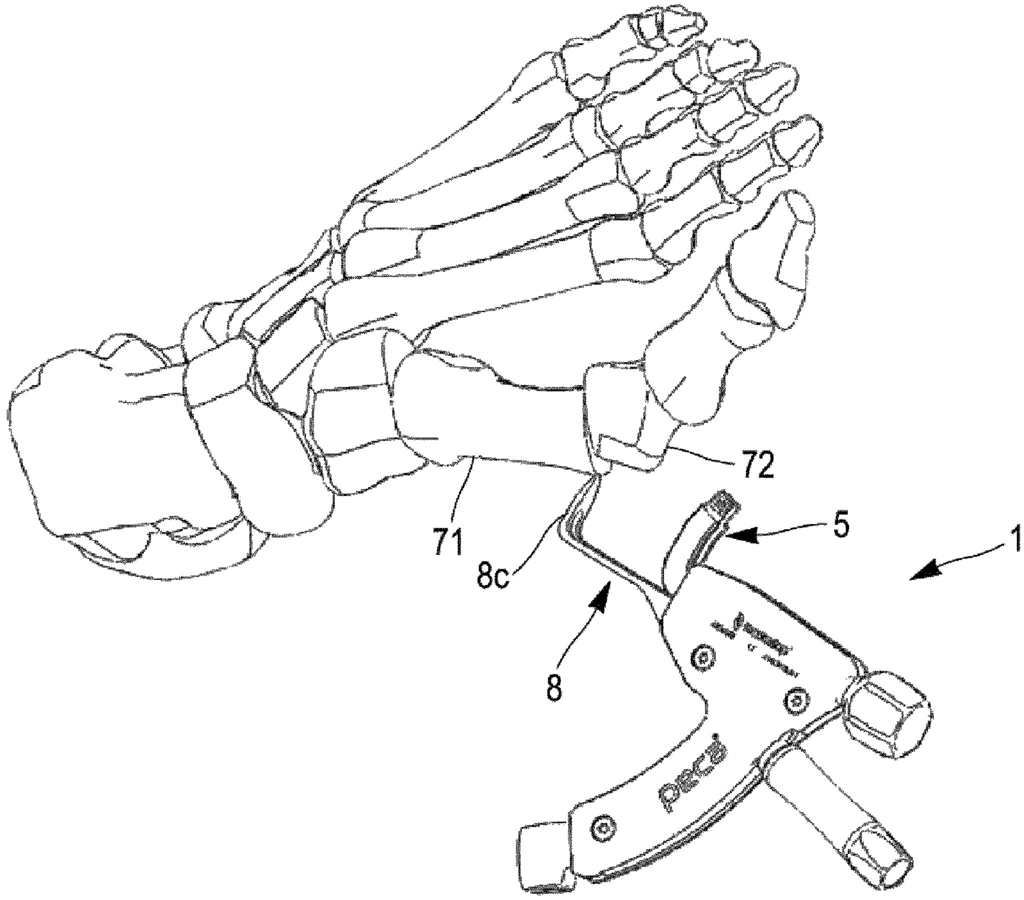

[Fig. 31B]
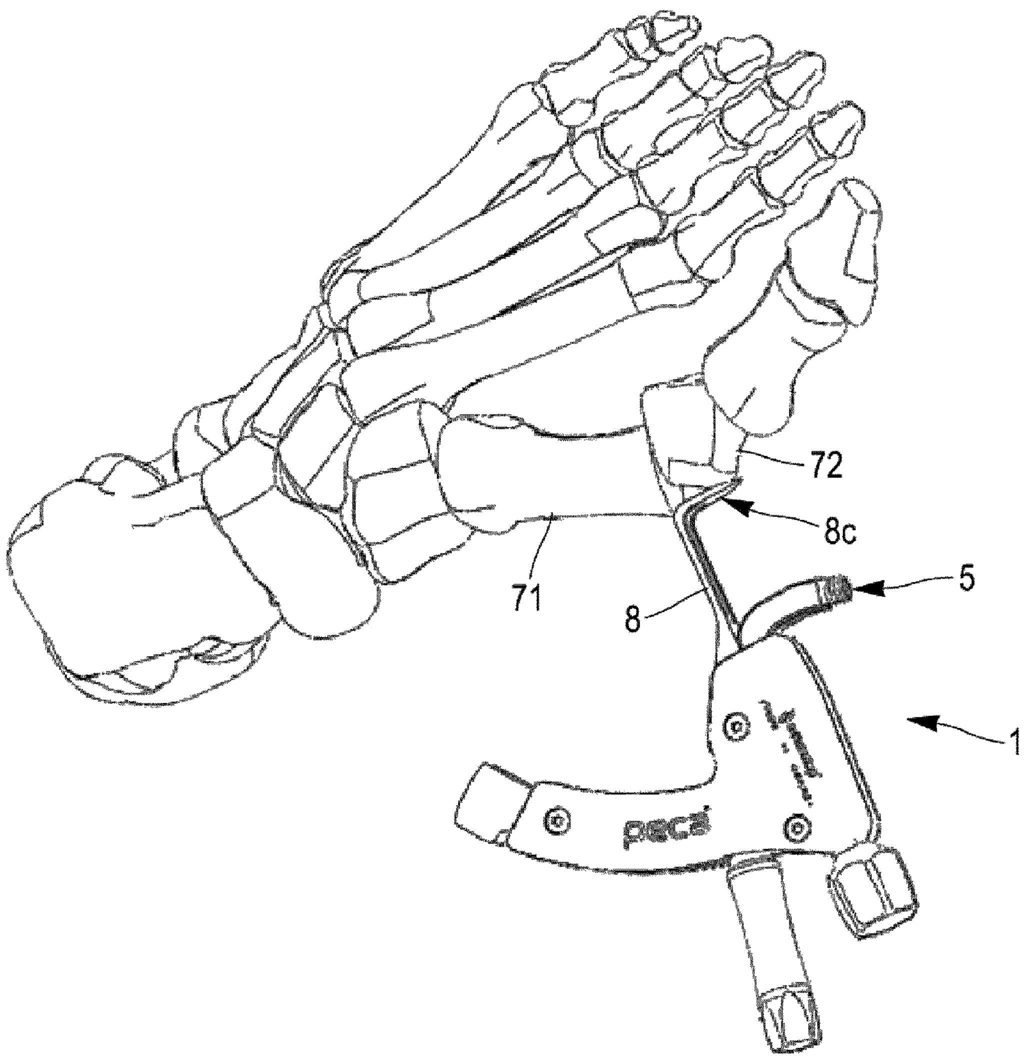

[Fig. 32A]
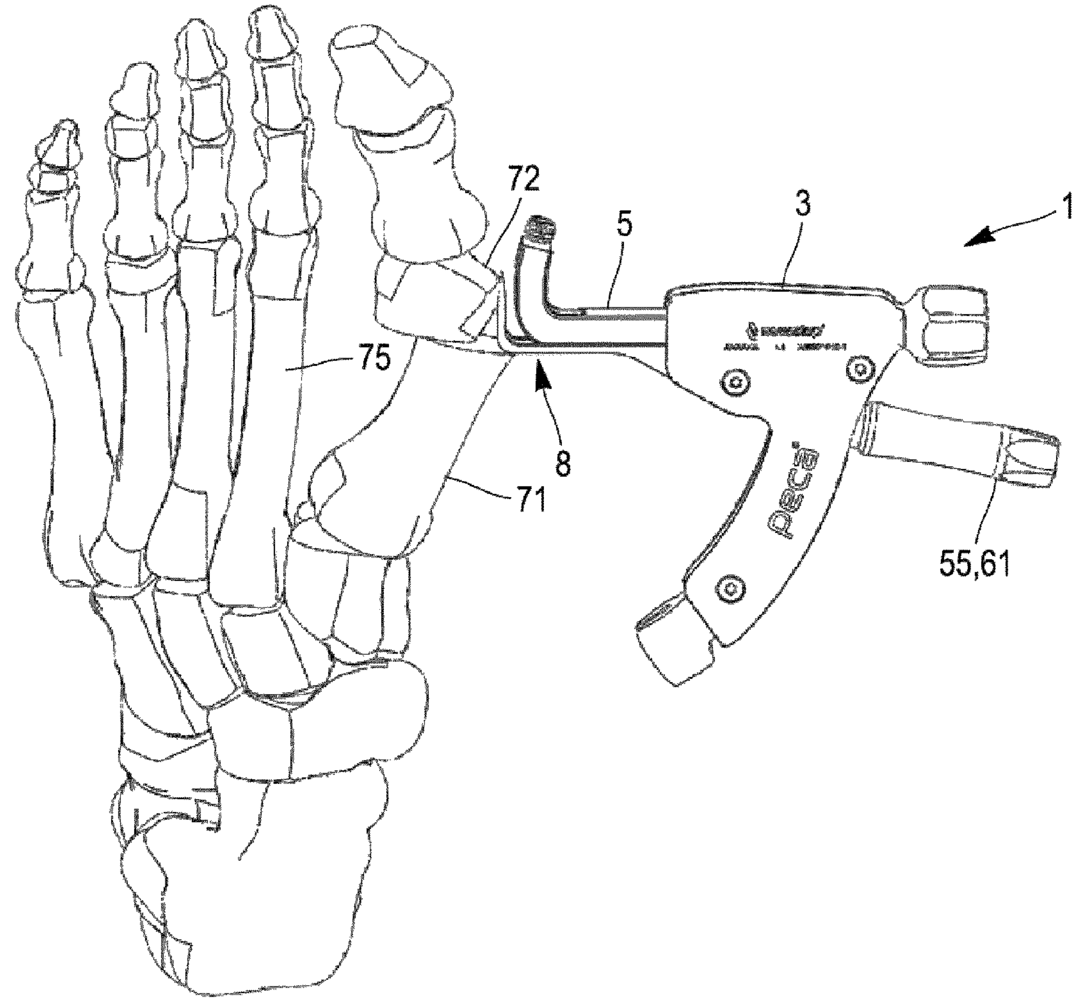
[Fig. 32B]
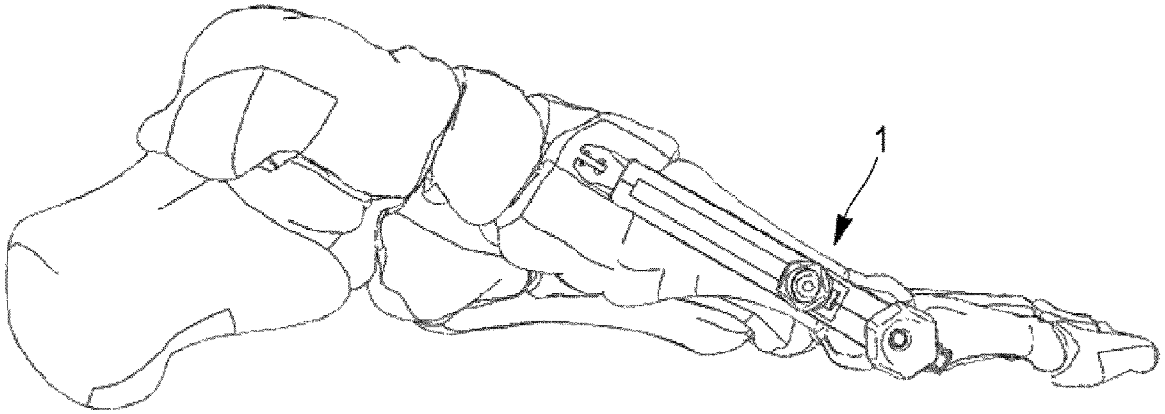

[Fig. 33A]
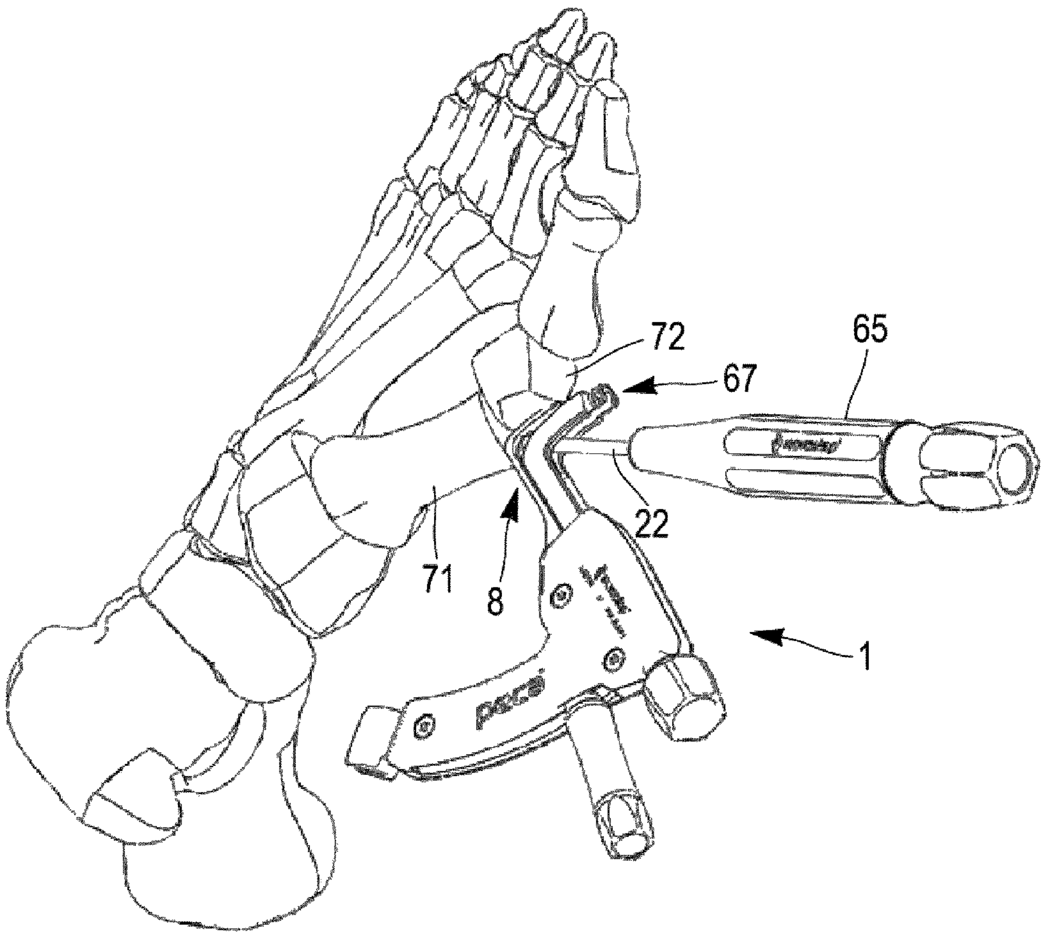

[Fig. 33B]
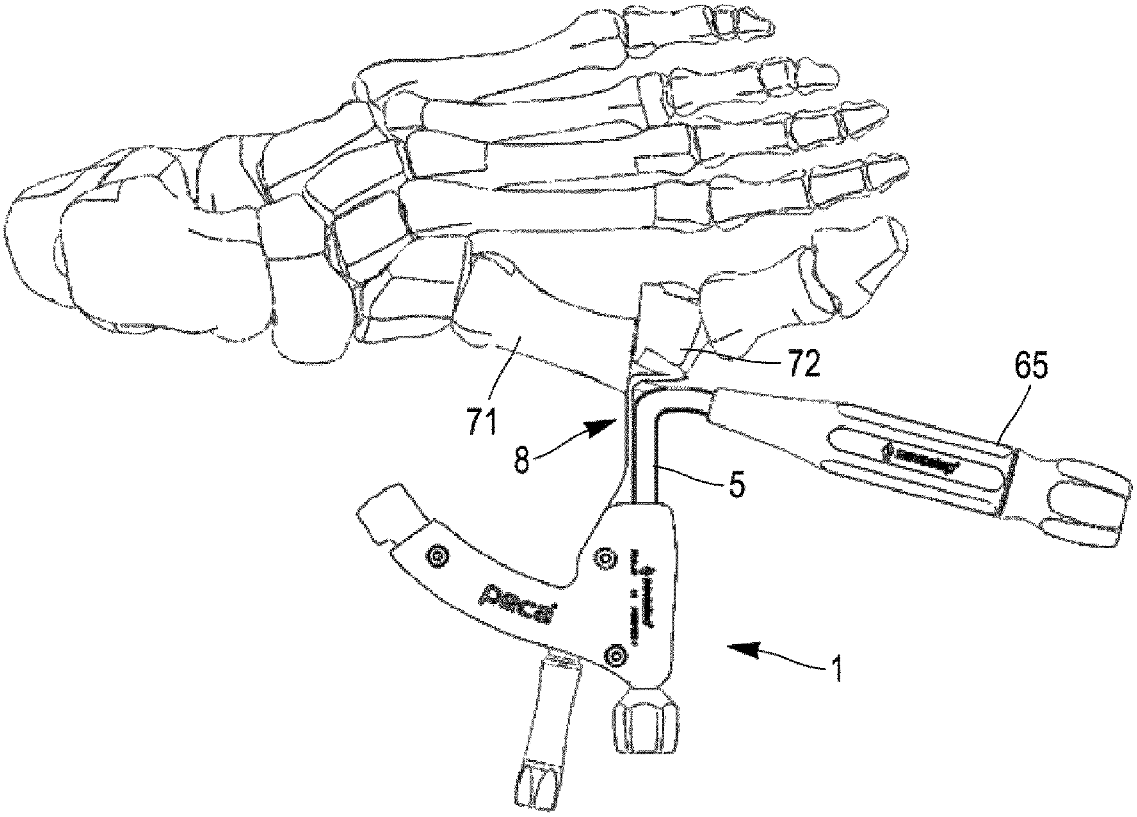

[Fig. 33C]
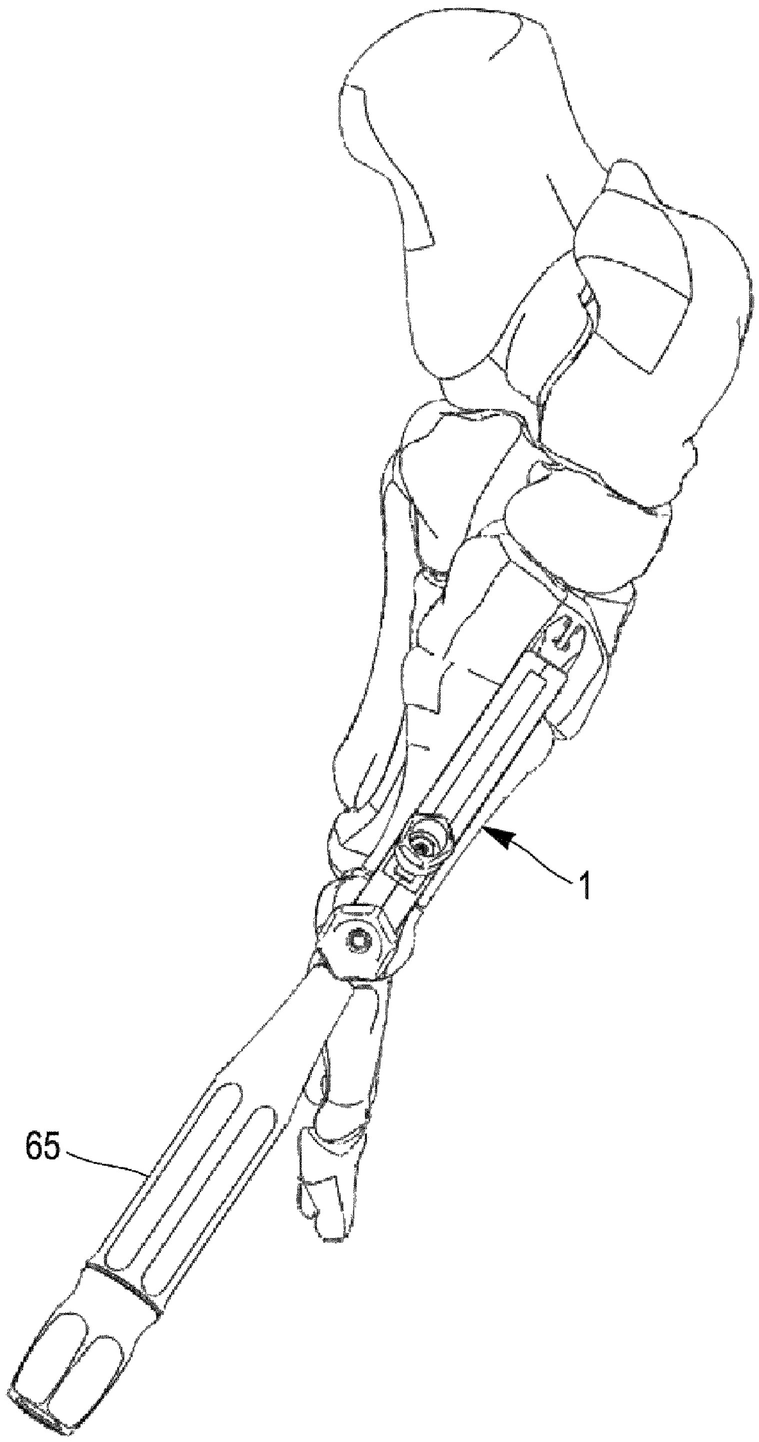

[Fig. 34A]
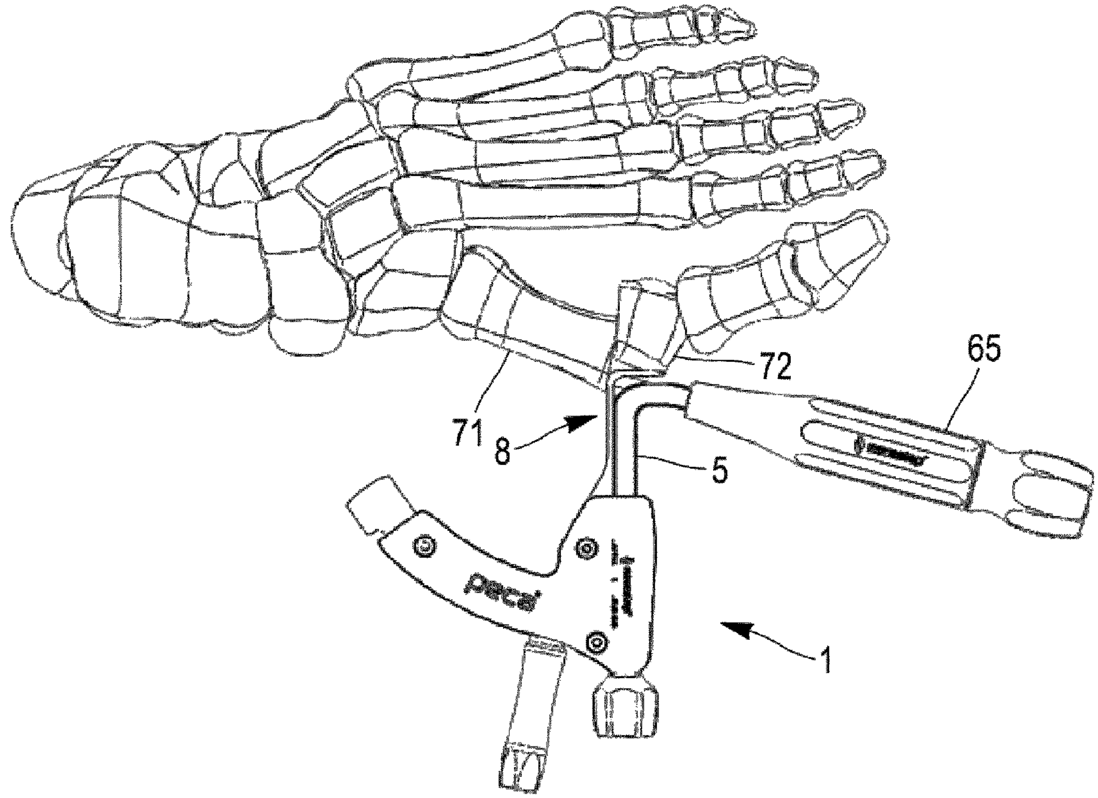
[Fig. 34B]
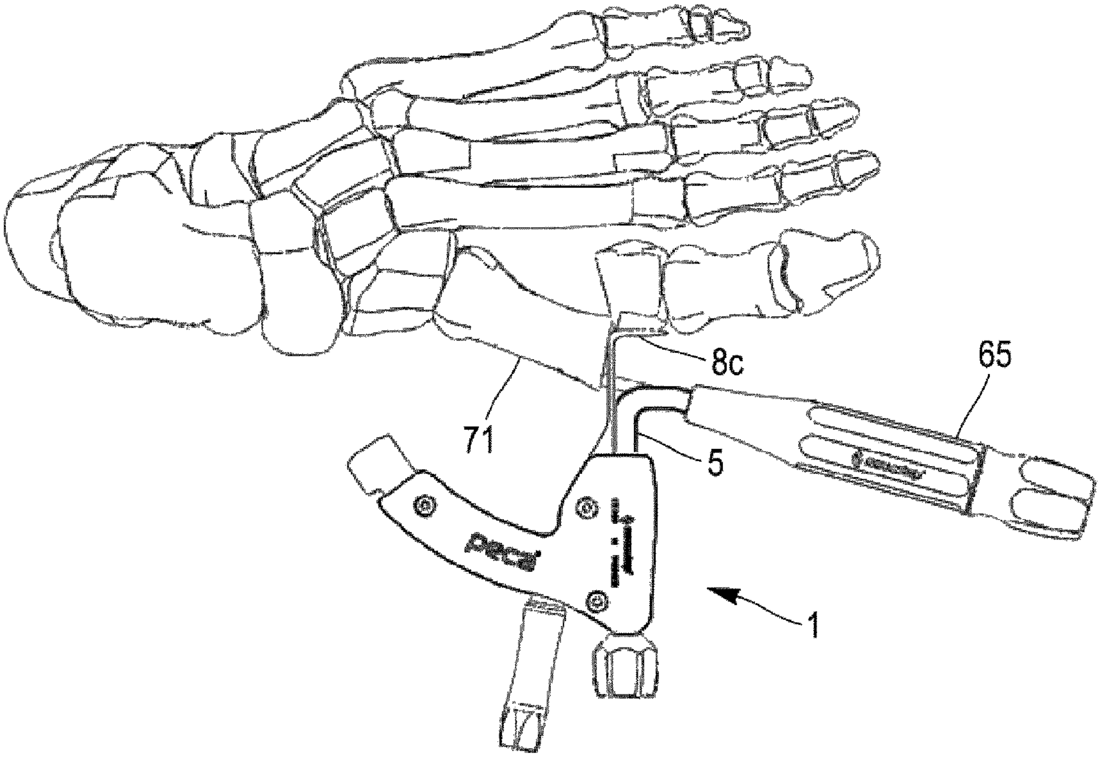

[Fig. 35]
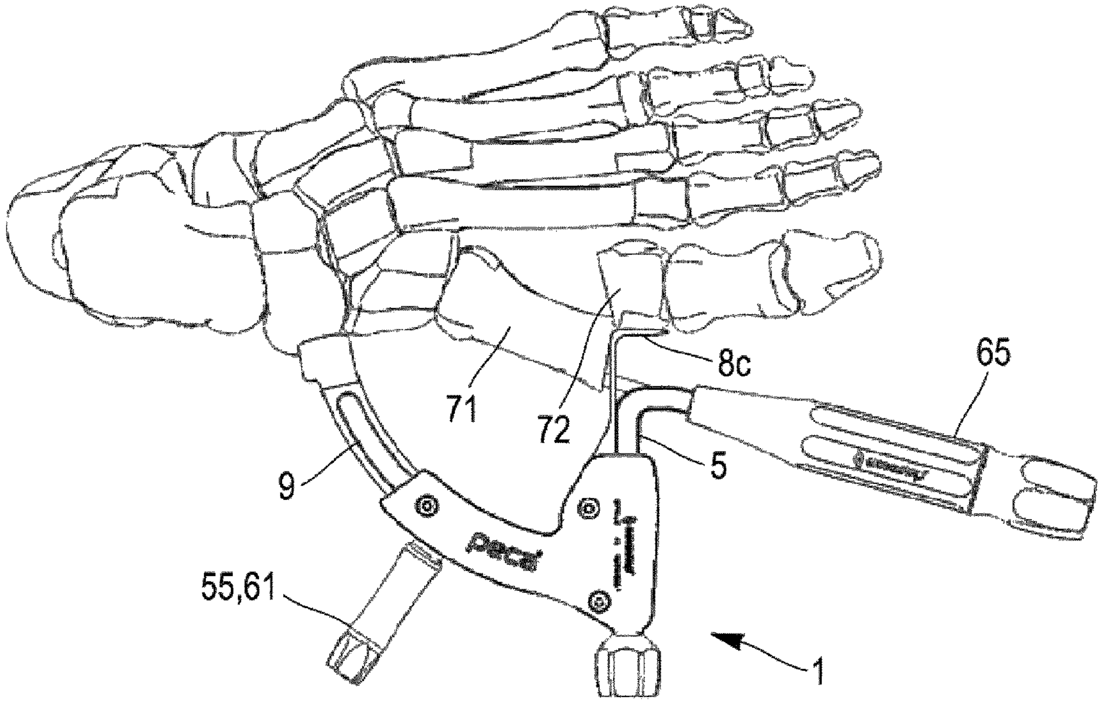
[Fig. 36A]
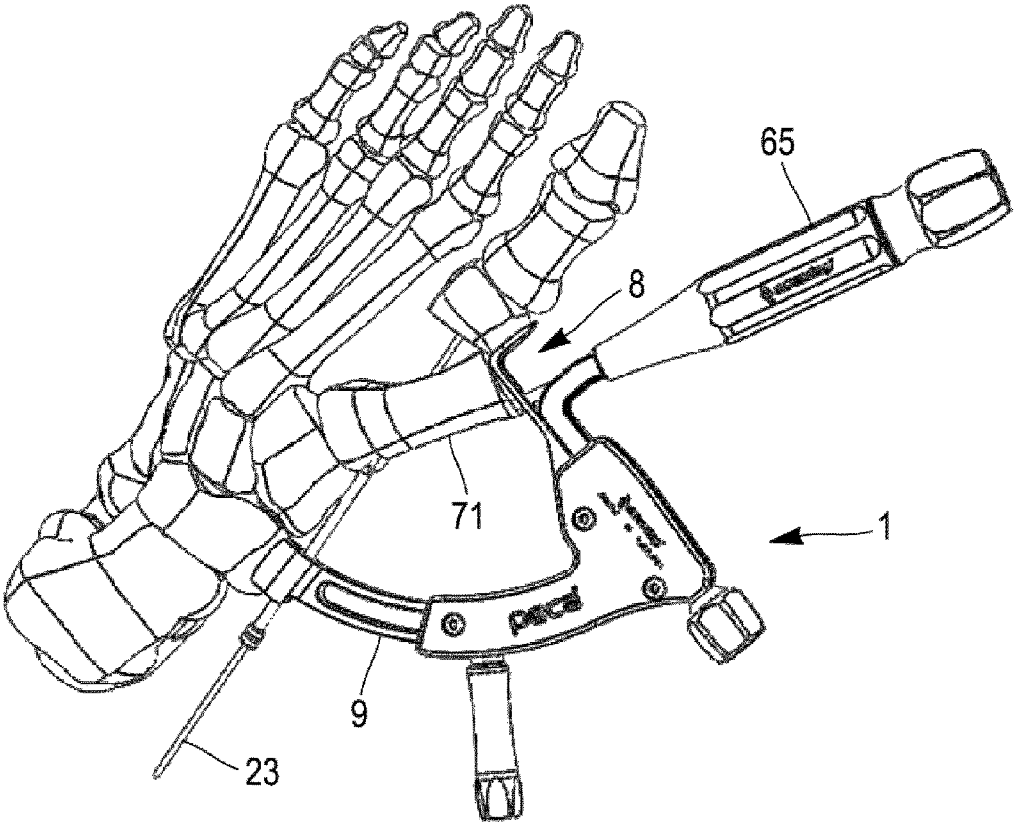

[Fig. 36B]
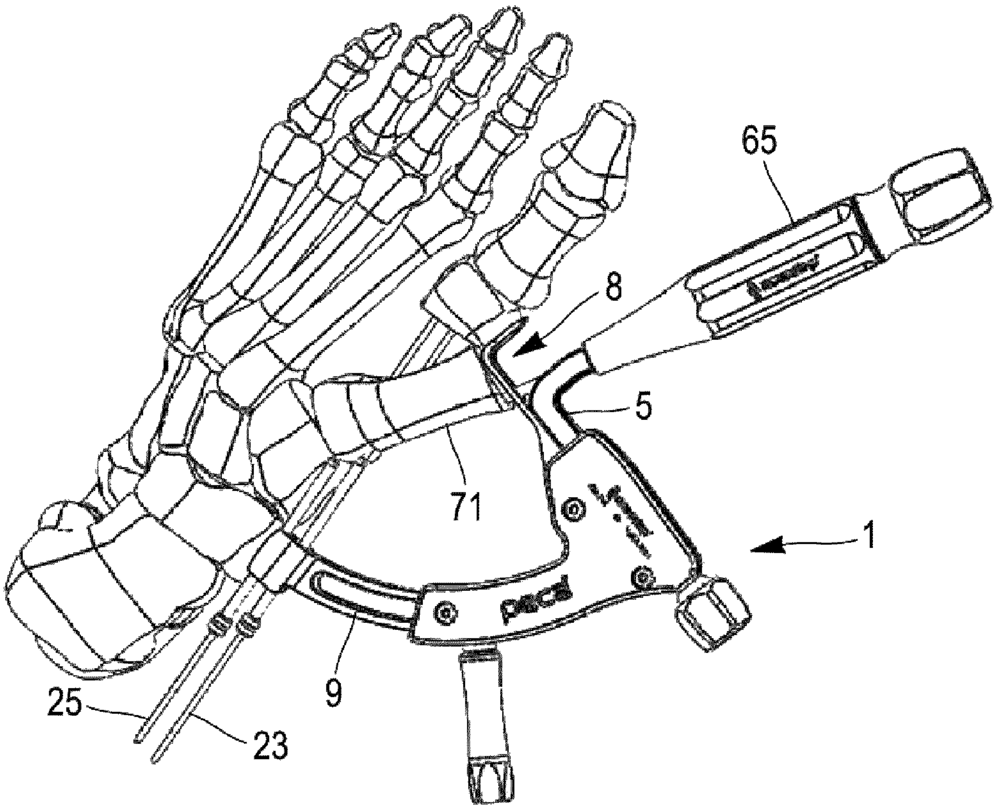

[Fig. 37A]
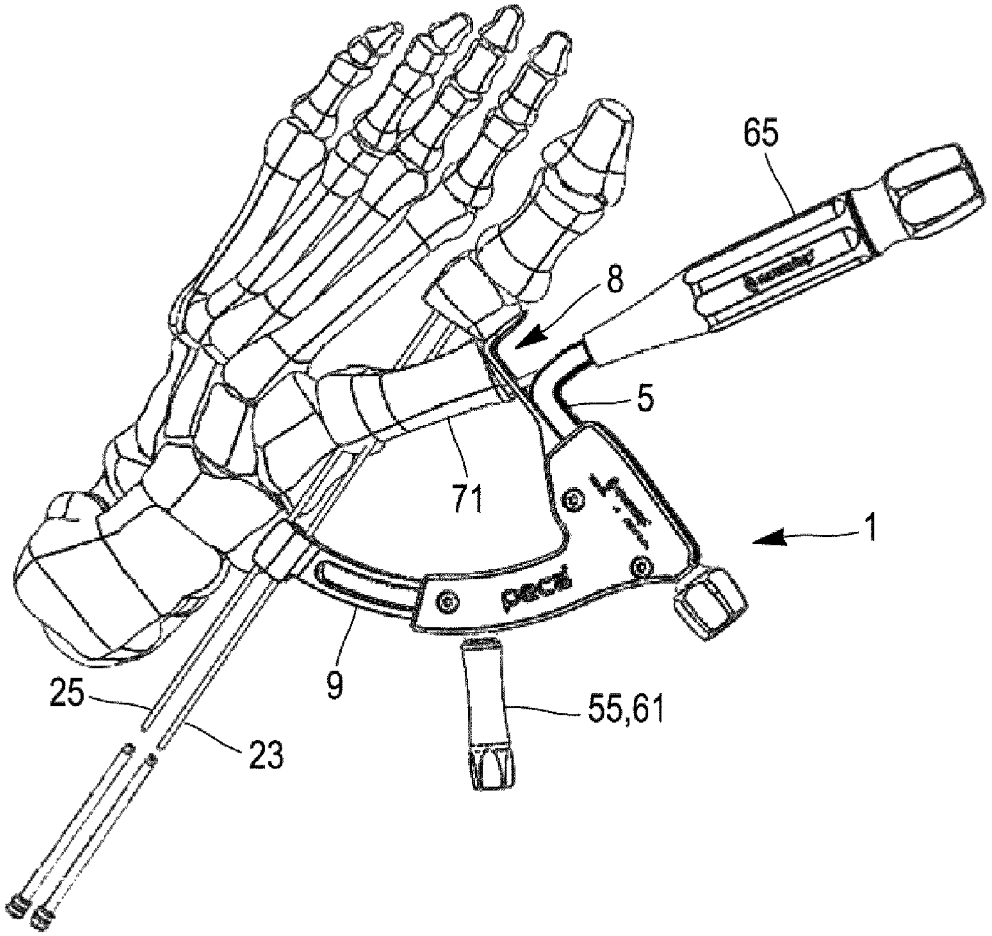

[Fig. 37B]
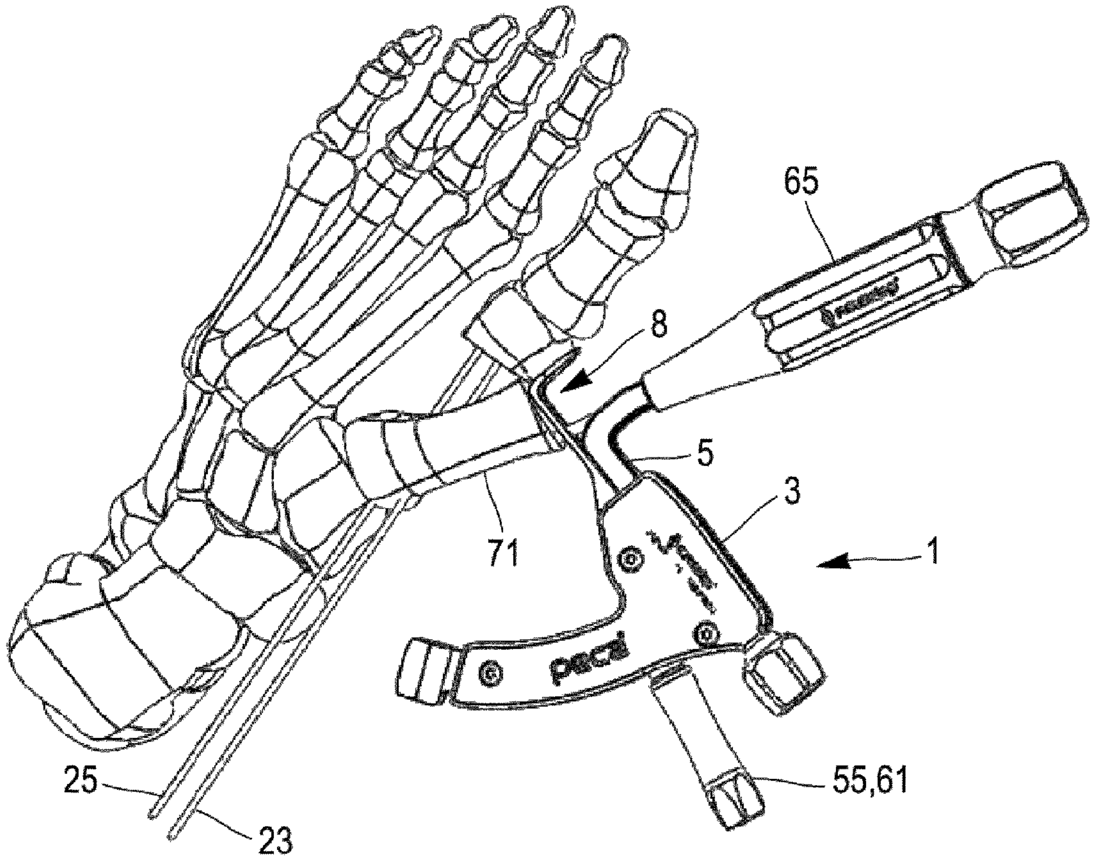

[Fig. 37C]
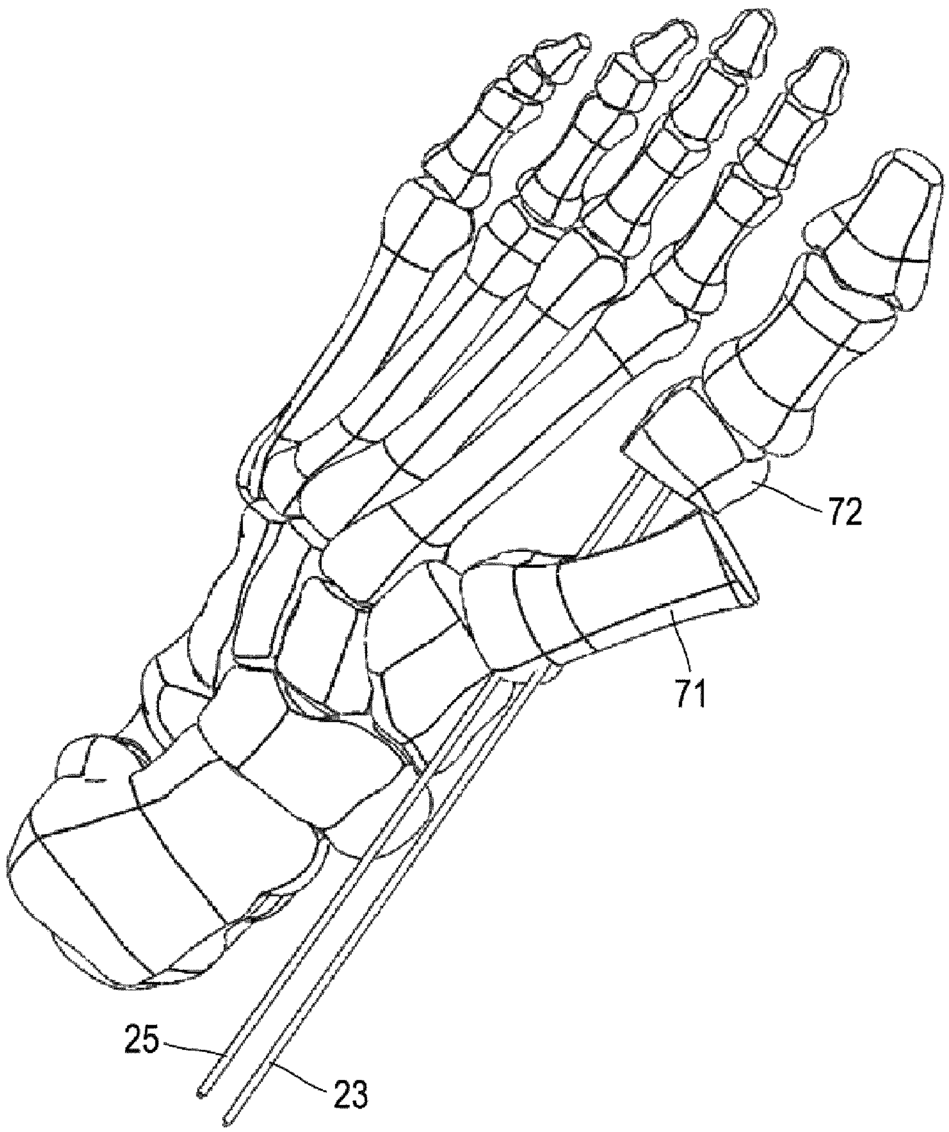

REUSABLE SURGICAL GUIDE FOR OSTEOSYNTHESIS SURGERY IN PARTICULAR OF THE HALLUX VALGUS AND METHOD OF USING THE SAME

TECHNICAL FIELD

The present invention concerns the field of surgical guides and method of using the same. More particularly, the instant disclosure relates to a reusable surgical guide for osteosynthesis surgery of the hallux valgus, in particular, in mini-invasive or percutaneous approach. By mini-invasive approach, it should be understood a surgery limiting the approach accesses to a few centimeters and by percutaneous approach, it should be understood a surgery limiting approach accesses to a few millimeters.

STATE OF THE ART

It is well known that the deformation of the hallux valgus results from a cuneiform-metatarsal hypermobility upon a metartarsus varus. The metatarsus varus is accentuated at the bearing phase. There is then observed an inward deviation, called varus of the first metatarsal, whereas the first phalanx, retained by its joint capsule and the sesamoidal line, deviates outwards, which is called valgus.

There are different surgical techniques allowing correcting this deformation. All these surgical techniques include at least four essential steps contributing to the durability of the correction: the lateral release of the sesamoidal line which allows releasing the retracted tissues and enables the mobilization of the first phalanx; the osteotomy of the first metatarsal (Scarf, Chevron, Bosch, . . . ) which contributes to the reduction of the angle between the first and second metatarsi and to the resection of the inflamed areas; the osteotomy of the first phalanx necessary to the recovery of the M1/P1 alignment; and the capsulorrhaphy of the joint playing a key role in holding of the correction. It should be noted that, in the percutaneous approach, this last step is irrelevant, the joint capsule being perforated a few millimeters.

In the context of a mini-invasive or percutaneous approach surgery in the correction of the hallux valgus, one amongst the commonly used techniques is called PECA (registered trademark) standing for «Percutaneous Chevron-Akin» and consists in the stabilization of the two bone fragments of the metatarsus by means of two screws inserted in parallel.

In contrast with a «Scarf» or «Chevron» hallux valgus correction, the technique differs essentially by the increase of the varus of the first metatarsus to perform the translation of the distal fragment, the DMAA standing for «Distal Metatarsal Articular Angle» then being forced. Hence, the axis of the head describes an acute angle with respect to the axis of the diaphysis of the first metatarsus.

During the surgery, the position of the first wire, the proximal wire, is the most decisive step and also the most complex to carry out. Indeed, the proper position and orientation of this wire will determine the stability of the primary mounting and also the placement of the second wire and then of the screws which will achieve the osteosynthesis.

The proximal wire shall be placed in the proximal portion of the first metatarsus, cross the two cortical portions of the bone before ending in the distal fragment made during the osteotomy and the translation. By the anatomy variety in humans, the angle of the wire differs for each individual, each osteotomy and each translation. The surgeon shall then adapt the trajectory of the proximal wire to each surgery.

A second wire, the distal wire, shall be inserted parallel to the proximal wire, with an interspace that shall be neither too large nor too small. The two wires serving as a guide for the upcoming osteosynthesis screws, the screws shall be neither too far so that both reach the distal fragment, nor too close, in order to avoid a deterioration of the screws during the insertion because of interference between the screws. Alternatively, the distal (medial) wire may be placed first and the proximal (lateral) wire placed second.

Usually, the wires insertion steps are performed under radioscopy. Hence, the X-ray images are numerous which might be harmful to the health of the patients and of the radiographers. In addition, in most cases, the wires are not parallel which results in an improper positioning of the screws, a possible mechanical weakness of the system and therefore a failure of the surgery.

In order to overcome these drawbacks, several systems allowing guiding these wires have already been imagined. It is the case in particular of the international patent application WO2017/040843 and of the American patent application US2020/0060698, commercialized, mainly by the company Wright Medical with the MICA system, a registered trademark, standing for «Mini-invasive Chevron-Akin».

The document WO2017/040843 describes chevron osteotomy tools and methods and, more particularly, an aimer guide which comprises a handle extending substantially along a longitudinal axis. The longitudinal handle delimits one or several burr hole(s) extending from a first side of the handle to a second side of the handle. A head is coupled to a distal end of the longitudinal handle. The head delimits a plurality of guide holes sized and designed so as to receive a Kirschner wire therethrough. Thus, this system consists of a single-piece guide whose distal end is inserted onto a percutaneous drill positioned beforehand at the level of the osteotomy site. Afterwards, the practitioner selects the most suited window in the proximal portion of the guide to direct his first wire based on several radiographic images. The same operation is replicated for the second wire.

Although allowing assisting the surgeon to properly direct his wires, this guide type has the drawback of not enabling an intuitive use, of not enabling the wires angle variation that is necessary to the proper translation of the epiphysis of the metatarsus and of not systematically preventing the risk of interference during the insertion of the screws. Moreover, the use of several radiographic images is still necessary.

The American patent application US2020/0060698 describes an aimer guide comprising a body defining a first guide hole sized and configured to receive a guide sleeve therethrough. The first guide hole extends through the body on a first axis. An alignment arm extends between a first end and a second end. The first end is coupled to the body. A tip extends from the second end of the alignment arm. A free end of the tip is aligned with the first axis of the first guide hole. Thus, the system is composed by a guide accompanied with guide barrels for wires. The practitioner inserts the distal end of the guide into the osteotomy and positions the touch-probe at the desired exit point of his first wire. This operation is performed again based on several radiographic images. The first barrel is positioned in the proximal area of the guide thereby allowing guiding the first wire. The same operation is replicated for the second wire. This second system allows marking the exit point of the first wire beforehand and therefore guaranteeing the trajectory while minimizing the options of parallel windows preventing the risk of interference during the insertion of the upcoming screws.

Nevertheless, its use still requires radiographic images and the defective adhesion with the metatarsal requires gestures that are complex for the practitioner in order to hold the guide in the desired position while inserting the wires.

SUMMARY

Hence, one amongst the objects of the invention is to overcome these drawbacks by providing a surgical guide for osteosynthesis surgery with a simple and inexpensive design, allowing limiting the number of radiographic images, simplifying the gestures of the surgeon during the surgery and preventing the risk of interference during the insertion of the screws.

To this end, and in accordance with the invention, there is provided a reusable surgical guide for osteosynthesis surgery, for the insertion of positioning wires into bone portions, characterized in that it comprises a grip comprising a head extending at one end a base, a blade secured to the head extending in the continuation of the head, a trigger configured to cooperate with a first slide formed in the head of the grip so as to be displaced relative to the grip along the blade, the trigger comprising a guide element for the insertion of a pull wire, and an aiming piece configured to cooperate with a second slide formed in the base of the grip so as to be displaced relative to the grip, said aiming piece comprising at its distal end a means for supporting at least one positioning wire.

In other words, there is provided a reusable surgical guide for hallux valgus, forming an aimer for guiding and inserting axial wires into bone portions; said surgical guide is remarkable in that it comprises a grip comprising a head extending at the upper end of a base, a trigger adapted to be displaced in a first slide formed in the head of the grip and whose distal end is provided with a through hole for the insertion of a wire, a blade secured to the distal end of the head of the grip, under the trigger, and a so-called aiming piece adapted to be displaced in a second slide formed in the base of the grip, said aiming piece comprising at the distal end thereof means for supporting at least one wire.

It is understood that, although the surgical guide according to the invention aims at one unique point like the surgical guides of the prior art, the guide according to the invention aims at an extrapolated unique point that is located on the moving distal fragment.

Thus, the instrumentation according to the invention adapts to the translation applied by the surgeon and therefore avoids under-corrections and over-corrections and their related problems.

For example, the guide element is a through hole.

According to one variant, said grip is constituted by two half-shells respectively comprising a bent head and branch whose concavity is directed towards the distal end of the trigger and whose lower end is open for the passage of the so-called aiming piece, the head and the bent branch being provided with through holes, extending opposite one another in pairs.

Preferably, the base has a circular-arc shape whose concavity is directed towards the distal end of the head of said grip.

Said base of the grip comprises a flat surface and two bent parallel branches, each branch being provided with at least two through holes, extending opposite one another in pairs.

In some embodiments, the surgical guide comprises an assembly for holding the position of the aiming piece, the holding assembly comprising a blocking element configured to cooperate with the aiming piece so as to block a movement of the aiming piece, and an element for actuating the blocking element configured to displace the blocking element in contact or remotely from the aiming piece. This allows holding the position of the aiming and therefore limiting the risk of displacement of the aiming piece during the insertion of the at least one positioning wire. Hence, positioning of the at least one positioning wire is more accurate.

Moreover, the so-called aiming piece has a circular-arc shape.

Said aiming piece has an aperture extending substantially from the proximal end up to the distal end of the aiming piece, said aperture enabling the passage of screws cooperating with the holes of the bent branches of the grip.

In addition, the means for supporting the at least one positioning wire comprises at least one cylindrical sleeve whose axis of revolution extends in the sagittal plane of the guide, in the direction of the distal end of the blade, said cylindrical sleeve forming a sheath adapted to receive a barrel for aiming the at least one positioning wire.

Advantageously, the sheath includes a longitudinal slot, said slot extending in the sagittal plane of said guide.

According to one variant, the means for supporting the at least one positioning wire comprises two substantially parallel cylindrical sleeves whose axes of revolution extend in the sagittal plane of the guide, in the direction of the distal end of the blade, said cylindrical sleeves forming first and second sheaths adapted to receive a barrel for aiming first and second wires, respectively.

Incidentally, the trigger comprises a measuring graduation.

Moreover, said blade has an L-like general shape and comprises a proximal portion extending parallel to the head of the grip and provided with a longitudinal aperture and a distal portion adapted to bear on the epiphysis of the metatarsus.

According to one variant, said blade has a rectilinear shape and comprises a proximal portion extending parallel to the head of the grip and provided with a longitudinal aperture.

Advantageously, the surgical guide according to the invention includes a means for pulling the trigger.

The means for pulling the trigger comprises a worm screw a first end thereof cooperates with said trigger and the opposite end thereof is provided with a knob.

Incidentally, the surgical guide according to the invention includes a rack with an unlock button to ensure translation of the head and holding of the correction.

In some embodiments, the guide element of the trigger is configured to enable the pivoting of the pull wire in the sagittal plane of the surgical guide.

For example, the through hole of the trigger is open so as to enable the pivoting of the pull wire in the sagittal plane of the surgical guide.

In some embodiments, the trigger comprises a holding element intended to hold the pull wire on the trigger.

For example, the distal end of the trigger comprises a threaded portion, configured to cooperate with a grip for supporting the pull wire, so as to fasten the support grip on the trigger.

This disclosure also relates to a method for operating a surgical guide including positioning the surgical guide adjacent to a first bone, the first bone including a cut surface dividing the first bone into a first bone portion and a second bone portion; inserting the draw wire into the first bone portion and into the through hole in the distal end of the trigger; retracting the trigger in a proximal direction through the first slide in a state in which the draw wire extends through the through hole and into the first bone portion such that the first bone portion is moved relative to the second bone portion; and then inserting a first wire through the supporting means and into the first bone portion and the second bone portion to fix the first bone portion to the second bone portion, the first wire being inserted in a state in which the surgical guide together with the draw wire holds relative positions of the first bone portion and the second bone portion.

BRIEF DESCRIPTION OF THE DRAWINGS

Other advantages and features will appear better from the following description of several variants, provided as non-limiting examples, of the surgical guide in accordance with the invention, with reference to the appended drawings wherein:

FIG. 1 is a perspective view of the surgical guide according to the invention, FIG. 2 is an exploded perspective view of the surgical guide according to the invention, FIG. 3 is an exploded perspective view of the grip of the surgical guide according to the invention, FIG. 4 is an exploded perspective view of the aiming piece sliding in the grip of the surgical guide according to the invention, FIG. 5 is an exploded perspective view of the grip of the surgical guide according to the invention, FIG. 6 is a sagittal sectional view of the surgical guide according to the invention, FIGS. 7 to 11 are side views of the surgical guide according to the invention at the different steps of use of said surgical guide, FIG. 12 is a perspective view of the surgical guide according to the invention after placement of a first wire in the first metatarsus, FIG. 13 is a side view of the placement of the second wire by means of a second so-called parallel guide, FIG. 14 is a side view of a variant of the surgical guide according to the invention, FIGS. 15 and 16 are side views of the variant of the surgical guide according to the invention at the different steps of use of said surgical guide, FIG. 17 is a perspective view of a second variant of the surgical guide according to the invention, FIG. 18 is a sagittal sectional view of the second variant of the surgical guide according to the invention represented in FIG. 17, FIG. 19 is a perspective view of a third variant of the surgical guide according to the invention, FIG. 20 is a sagittal sectional view of the third variant of the surgical guide according to the invention represented in FIG. 19, FIG. 21 is an exploded perspective view of the third variant of the surgical guide according to the invention represented in FIGS. 19 and 20, FIG. 22 is a perspective view of a fourth variant of the surgical guide, FIG. 23 is a perspective view of a fourth variant of the surgical guide, FIG. 24 is a sectional view of a fourth variant of the surgical guide, FIG. 25 is a perspective view of a fourth variant of the surgical guide, FIG. 26 is a perspective view of a fourth variant of the surgical guide, FIG. 27 is a perspective view of a fourth variant of the surgical guide, FIGS. 28A and 28B are a perspective view of a patient's foot being prepared for an osteotomy, FIGS. 29A-C illustrate a preliminary shift using the draw wire, FIGS. 30A-D illustrate a method of preparing the surgical guide, FIGS. 31A and 31B show positioning the surgical guide relative to the metatarsal, FIGS. 32A and 3B show orienting the surgical guide relative to the metatarsal, FIGS. 33A-33C show insertion of the pull wire and arrangement within the surgical guide, FIGS. 34A-34B show translation of the first and second bone portions using the surgical guide, FIG. 35 shows deployment of the aiming piece, FIGS. 36A and 36B show insertion of the positioning wires using the surgical guide, and FIGS. 37A-37C show removal of the guide after the positioning wires have been placed.

DETAILED DESCRIPTION

In the following description of the surgical guide according to the invention, the same reference numerals refer to the same elements. The different views are not necessarily plotted to scale. Moreover, the surgical guide according to the invention is particularly suited to an osteosynthesis of a hallux valgus but it is quite obvious that it could be suited to the osteosynthesis of any other portion of the anatomy of the human body yet without departing from the scope of the invention.

Referring to FIGS. 1, 2 and 6, the surgical guide 1 according to the invention comprises a grip 2 comprising a head 3 extending at the upper end of a base 4, a trigger 5 adapted to be displaced in a first slide 6 formed in the head 3 of the grip 2 and whose distal end is provided with a guide element, in this instance, a through hole 7 for the insertion of a wire, not represented in FIGS. 1 and 6, a blade 8 secured to the distal end of the head 3 of the grip 2, under the trigger 5, said blade 8 having an L-like general shape and comprising a proximal portion 8*a* extending parallel to the head 3 of the grip 2 and provided with a longitudinal aperture 8*b* and a distal portion 8*c* adapted to bear on the epiphysis of the metatarsus, and a so-called aiming piece 9 adapted to be displaced in a second slide 10 formed in the base 4 of the grip 2, said aiming piece 9 comprising at its distal end at least one means 11 for supporting at least one positioning wire.

Referring to FIGS. 1 to 6, the base 4 of the grip 2 has a circular-arc shape whose concavity is directed towards the distal end of the blade 8. Said base 4 of the grip 2 comprises a flat surface 12 and two bent parallel branches 13, each branch 13 being provided with at least two through holes 14, extending opposite one another in pairs. The head 3, which has a substantially parallelepipedic shape, is screwed on the flat surface 12 by means of two screws 15 cooperating with two threaded holes 16 formed on said flat surface 12.

Moreover, the so-called aiming piece 9 has a circular-arc shape having the same radius of curvature as the base 4 of the grip 2. Said aiming piece has an aperture 17 extending substantially from the proximal end up to the distal end of the aiming piece 9, said aperture 17 enabling the passage of screws 18 cooperating with the holes 14 of the bent branches 13 of the grip 2.

It is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

In addition, the support means 11 comprises at least one cylindrical sleeve 19 whose axis of revolution extends in the sagittal plane of the surgical guide, in the direction of the distal end of the blade 8, said cylindrical sleeve 19 forming a sheath adapted to receive a barrel 20 for aiming a positioning wire. Advantageously, the sheath formed by the cylindrical sleeve 19 includes a longitudinal slot 21, at the proximal end of the support means 11, said slot 21 extending in the sagittal plane of said guide, so as to enable an easy removal of the surgical guide after set-up of the positioning wire, the aiming barrel being removed beforehand, the positioning wire then passing through said slot 21.

The operation of the surgical guide according to the invention will now be explained with reference to FIGS. 7 to 13.

The practitioner incises by about 5 mm the skin and the joint capsule at the level of the bunion. Using a percutaneous drill, he performs the medial exostectomy (FIG. 7) of the metatarsus in order to reduce the arthritic areas as much as possible. Afterwards, he will perform the osteotomy of the epiphysis of the metatarsus thereby separating the head from the diaphysis. The practitioner inserts the blade 8 into the incision such that the distal end of the blade 8 bears against the medial edge of the head of the metatarsus (FIG. 7). A slight translation is already applied during this insertion. It should be noticed that as the blade 8 is easily removable with respect to the grip 2, it could also be inserted into the incision and then mounted on the grip 2.

Referring to FIG. 8, the practitioner then sets the trigger 5 in position against the blade 8 by simply pressing thereon to make it slide in the first slide 6. A stabilization/draw wire 22 may then be inserted into the intramedullary canal of the metatarsus through the hole 7 of the trigger 5 provided to this end, with reference to FIG. 9.

Once the draw wire 22 is set in place, with reference to FIG. 10, the practitioner could draw the diaphysis by pulling on the trigger 5. Thus, we find the principle of the surgical technique, which consists in increasing the varus of the metatarsus to translate the head. By drawing the diaphysis and holding the head of the metatarsus, a correction of the DMAA (Distal Metatarsal Articular Angle) is automatically performed.

Referring to FIGS. 11 and 12, by rotating the aiming piece 9, the practitioner selects the entry point of a first positioning wire 23 which shall be as proximal as possible. He inserts the first positioning wire 23 and could insert the second distal positioning wire 25 if the device is equipped with a double sheath as will be detailed later on.

The practitioner can now remove the aiming barrel 20 used to insert the so-called proximal first positioning wire 23, and then, by rotating the aiming piece 9, he clears the positioning wire 23 which then passes through the slot 21 and thus extract the surgical guide according to the invention while leaving the proximal positioning wire 23, stabilizing the system.

Referring to FIG. 13, the practitioner may be assisted by a parallel guide 24 to insert the second positioning wire 25, substantially parallel to the first proximal positioning wire 23. The practitioner could, if he so wishes, insert the first implant before inserting the second positioning wire 25. He will carry on the insertion of the second implant thereby totally fixing the system. Lastly, the practitioner will perform a last exostectomy to remove the bone wedge likely to aggress the soft tissues of the patient and hinder him when walking.

According to one variant, with reference to FIG. 14, the surgical guide 1 according to the invention comprises, in the same manner as before, a grip 2 comprising a head 3 extending at the upper end of a base 4, a trigger 5 adapted to be displaced in a first slide 6 formed in the head 3 of the grip 2 and whose distal end is provided with a guide element, in this instance, a through hole 7, for the insertion of a pull wire, not represented in FIGS. 1 and 6, and a so-called aiming piece 9 adapted to be displaced in a second slide 10 formed in the base 4 of the grip 2, said aiming piece 9 comprising at the distal end thereof a means 11 for supporting at least one positioning wire.

The base 4 of the grip 2 has a circular-arc shape whose concavity is directed towards the distal end of the trigger 5 of said grip 2. Said base 4 of the grip 2 comprises a flat surface 12 and two bent parallel branches 13, each branch 13 being provided with at least two through holes 14, extending opposite one another in pairs. The head 3, which has a substantially parallelepipedic shape, is screwed on the flat surface 12 by means of two screws 15 cooperating with two threaded holes 16 formed on said flat surface 12.

Moreover, the so-called aiming piece 9 has a circular-arc shape having the same radius of curvature as the base 4 of the grip 2. Said aiming piece has an aperture 17 extending substantially from the proximal end up to the distal end of the aiming piece 9, said aperture 17 enabling the passage of screws 18 cooperating with the holes 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

The surgical guide differs from the previously-described one in that it does not include any blade 8, in that the trigger 5 comprises a measuring graduation 26 and in that the support means 11 comprise two substantially parallel cylindrical sleeves 19 whose axes of revolution extend in the sagittal plane of the guide, in the direction of the distal end of the trigger 5, said cylindrical sleeves 19 forming first and second sheaths adapted to receive a barrel 20 for aiming first and second positioning wires, respectively.

Thus, the exit point of the positioning wire, extrapolated beforehand, is then found by measurement of the depth of the completed osteotomy. The practitioner could, if he so wishes, use a depth gauge to perform this measurement.

The operation of this variant of the surgical guide will now be explained with reference to FIGS. 15 and 16.

In this embodiment, the practitioner does not translate the epiphysis of the metatarsus but rather the trigger of the instrumentation according to the invention. Afterwards, the practitioner can insert the guide positioning wire(s), using the aiming arc and a barrel attached on this arc. Hence, the use of the instrumentation according to the invention boils down, with reference to FIG. 15, to carrying out the osteotomy, measuring the depth of the osteotomy using a depth gauge, inserting the pull wire into the intramedullary canal of the metatarsus and performing an overlapping of the surgical guide according to the invention on the wire; then, with reference to FIG. 16, to reporting the depth measurement, inserting the screw guide positioning wires 23, 25, removing the surgical guide, translating the epiphysis and proceeding with a complete insertion of the positioning wires 23, 25.

It should be noted that the variant represented in FIGS. 1 to 13 may include a support means 11 comprising two parallel cylindrical sleeves 19 whose axes of revolution extend in the sagittal plane of the guide, in the direction of the distal end of the trigger 5, said cylindrical sleeves 19 forming first and second sheaths adapted to receive the barrel 20 for aiming first and second positioning wire, respectively, yet without departing from the scope of the invention.

According to a second variant, with reference to FIGS. 17 and 18, the surgical guide 1 according to the invention comprises, in the same manner as that described with reference to FIGS. 1 to 6, a sleeve 2 comprising a head 3 extending at the upper end of a base 4, a trigger 5 adapted to be displaced in a first slide 6 formed in the head 3 of the grip 2 and whose distal end is provided with a through hole 7 for the insertion of a pull wire 22 a blade 8 secured to the distal end of the head 3 of the grip 2, under the trigger 5, said blade 8 having an L-like general shape and comprising a proximal portion 8*a* extending parallel to the head 3 of the grip 2 and provided with a longitudinal aperture 8*b* and a distal portion 8*c* adapted to bear on the epiphysis of the metatarsus, and a so-called aiming piece 9 adapted to be displaced in a second slide 10 formed in the base 4 of the grip 2, said aiming piece 9 comprising at the distal end thereof a means 11 for supporting at least one positioning wire.

Said base 4 of the grip 2 has a circular-arc shape whose concavity is directed towards the distal end of the blade 8. Said base 4 of the grip 2 comprises two bent parallel branches 13, each branch 13 being provided with at least two through holes 14, extending opposite one another in pairs. The head 3, which has a substantially parallelepipedic shape, comprises two portions, each portion of the head 3 carrying a bent branch 13 forming the base 4 of the grip 2.

Moreover, the aiming piece 9 has a circular-arc shape having the same radius of curvature as the base 4 of the grip 2. Said aiming piece 9 has an aperture 17 extending substantially from the proximal end up to the distal end of the aiming piece 9, said aperture 17 enabling the passage of screws 18 cooperating with a hole 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

In addition, the support means 11 comprises two cylindrical sleeves 19 whose axes of revolution extend parallel to one another in the sagittal plane of the surgical guide, in the direction of the distal end of the blade 8, said cylindrical sleeves 19 forming first and second sheaths adapted to receive a barrel for aiming the first and second positioning wires. Advantageously, the sheaths formed by the cylindrical sleeves 19 include a longitudinal slot 21, at the proximal end of the support means 11, said slot 21 extending in the sagittal plane of said guide, so as to enable an easy removal of the surgical guide after set-up of the positioning wires, the aiming barrel being removed beforehand, the wire then passing through said slot 21.

The surgical guide differs from the previously-described one in that it includes a means for pulling the trigger 5 comprising a worm screw 27 a first end thereof cooperates with said trigger 5 and the opposite end thereof is provided with a knob 28. In this manner, once the translation of the head is performed by the practitioner, the surgeon has freehand to manage the dorsoplantar position of the translated epiphysis of the metatarsus. With the other hand, he can insert the positioning wires, these therefore lying in the midplane of the head.

Incidentally, to ensure translation of the head and holding of the correction, a rack with an unlock button may be used.

According to a third variant, with reference to FIGS. 19 to 21, the surgical guide 1 according to the invention comprises, in the same manner as that described with reference to FIGS. 1 to 6, a grip 2 comprising a head 3 extending at the upper end of a base 4, a trigger 5 adapted to be displaced in a first slide 6 formed in the head 3 of the grip 2 and whose distal end is provided with a through hole 7 for the insertion of a pull wire, a blade 8 secured to the distal end of the head 3 of the grip 2, under the trigger 5, and a so-called aiming piece 9 adapted to be displaced in a second slide 10 formed in the base 4 of the grip 2, said aiming piece 9 comprising at the distal end thereof a means 11 for supporting at least one positioning wire.

The support means 11 comprises two cylindrical sleeves 19 whose axes of revolution extend parallel to one another in the sagittal plane of the surgical guide, in the direction of the distal end of the blade 8, said cylindrical sleeves 19 forming first and second sheaths adapted to receive a barrel for aiming first and second positioning wires, respectively. Advantageously, the sheaths formed by the cylindrical sleeves 19 include a longitudinal slot 21, at the proximal end of the support means 11, said slot 21 extending in the sagittal plane of said guide, so as to enable an easy removal of the surgical guide after set-up of the positioning wires, the aiming barrel being removed beforehand, the positioning wires then being configured to pass through said slot 21.

In the same manner as before, the surgical guide includes a means for pulling the trigger 5 comprising a worm screw 27 a first end thereof cooperates with said trigger 5 and the opposite end thereof is provided with a knob 28. In this manner, once the translation of the head is performed by the practitioner, the surgeon has freehand to manage the dorsoplantar position of the translated epiphysis of the metatarsus. With the other hand, he can insert the positioning wires, these therefore lying in the midplane of the head.

Incidentally, to ensure translation of the head and holding of the correction, a rack with an unlock button may be used.

The surgical guide differs from the previously-described one in that the grip 2 comprises two half-shells 29*a* and 29*b* respectively comprising a head 3 and a bent portion 13 whose concavity is directed towards the distal end of the trigger 5 and whose lower end is open for the passage of the aiming piece 9, the flat surface 12 and the bent branch 13 being provided with through holes 14, extending opposite one another in pairs. Thus, the head 3, which has a substantially parallelepipedic shape, is formed by two half-shells 29*a* and 29*b*.

Moreover, the aiming piece 9 has a circular-arc shape having the same radius of curvature as the base 4 of the grip 2. Said aiming piece 9 has an aperture 17 extending substantially from the proximal end up to the distal end of the aiming piece 9, said aperture 17 enabling the passage of screws 18 cooperating with the holes 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

The surgical guide also differs from the previously-described one in that said blade 8 has a rectilinear general shape rather than an L-like shape, and thus comprising only a proximal portion 8*a* extending parallel to the head 3 of the grip 2 and provided with a longitudinal aperture 8*b*.

In this third variant, the trigger 5 also comprises a measuring graduation 26.

A fourth variant of the surgical guide is represented in FIGS. 22 to 27.

This variant differs from the above-described variants in that the surgical guide comprises a holding assembly 51 for holding the position of the aiming piece 9. The holding assembly 51 comprises a blocking element 53 configured to cooperate with the aiming piece 9 so as to block the movement of the aiming piece 9, in particular, sliding of the aiming piece 9 in the slide 10 of the base 4. The holding assembly 51 further comprises an actuating element 55 for actuating the blocking element 53 allowing displacing the blocking element 53 in contact with or remotely from the aiming piece 9 so as to enable blocking or release of the aiming piece 9.

For example, the blocking element 53 comprises a tapped member 57 secured to the aiming piece 9. For example, the tapped member 57 is integral with the aiming piece 9. The blocking element 53 comprises a threaded portion 59, configured to cooperate with the tapped member 57. The actuating element 55 comprises an actuating handle 61. Thus, the rotation of the actuating handle 61 in one direction allows bringing the aiming piece 9 close to the actuating handle 61 and thus holding the aiming piece 9 against the slide 10 and the actuating handle 61 against the external wall of the base 4 of the grip 2. Hence, the movement of the aiming piece 9 relative to the slide 10 is prevented by friction. The rotation of the actuating handle 61 in the reverse direction enables the separation of the aiming piece 9 from the actuating handle 61, and thus releasing the movement of the aiming piece 9.

The fourth variant differs from the previous variants also in that the surgical guide comprises an element for holding the pull wire 22 on the trigger 5.

In the represented example, the holding element is a tapped portion 63 formed at the distal end of the trigger 5. In particular, the external surface of the distal end of the trigger 5 comprises the tapped portion 63. The tapping of the tapped portion 63 and the through hole 7 are substantially concentric. The tapped portion 63 is configured to cooperate with a threaded portion of a support grip 65 of the pull wire 22. Thus, the grip 65 for supporting the pull wire 22 could be locked by the trigger 5.

The fourth variant also differs from the previous variants in that the trigger 5 comprises a pivoting slot 67 of the pull wire 22. This allows inserting the pull wire 22 into the pivot slot 67 so as to reach the interior of the metatarsal more easily, as represented in FIG. 26, and then straightening the pull wire 22, by pivoting it in the sagittal plane of the guide.

In the represented example, the distal end of the trigger 5, and therefore the tapped portion 63, comprises the pivot slot 67 of the pull wire 22. Hence, the through hole 7 is open towards the head 3 by the pivot slot 67. In this instance, the pivot slot 67 enables pivoting of the pull wire 22 by an angle of about 60°. When the pull wire 22 is straightened, it is aligned with the distal end of the trigger 5 and with the through hole 7.

In this example, the longitudinal slot 8*b* of the blade 8 is extended in the bent down distal end 8*c* of the blade 8, in order to enable the passage and pivoting of the pull wire 22. The longitudinal slot 8*b* and the pivot slot 67 are superimposed.

The elements described with reference to one variant may be combined with elements described in other variants.

Moreover, it shall be emphasized that, regardless of the embodiment of the surgical guide according to the invention, the latter enables an accurate insertion of the first proximal positioning wire and that, regardless of the anatomy of the first metatarsus, an insertion of the second distal positioning wire parallel to the first proximal wire, without any risk of interference between the screws, a symmetrical use of the surgical guide according to the invention and a reduced use of radiographic images.

A method of using the surgical guide according to the present disclosure will now be explained with reference to FIGS. 28A-37C. Although the method is discussed herein using the surgical guide shown in FIGS. 22 to 27 (fourth variant), it will be appreciated that the method can be performed using any of the surgical guides disclosed herein.

Prior to the osteotomy, the contour of the first bone (e.g., first metatarsal) can be drawn with a marking pen. For instance, as shown in FIGS. 28A and 28B, a dermographic pen line running parallel to the dorsal surface of the first bone has been made. Then, a 4 mm incision that is centered at the osteotomy level is made along a part of the pen line. The percutaneous incision may be in the range of about 4 to about 5 mm in length. The incision is followed by a blunt dissection down to the underlying bone.

Then, an osteotomy to separate the first bone 70 into first and second bone portions 71, 72 can be performed. For example, an osteotomy of the epiphysis of the metatarsus can be performed by separating the head 72 from the diaphysis 71. A transverse osteotomy or any other suitable osteotomy can be performed, such as a chevron or modified chevron oriented osteotomy.

After the osteotomy has been performed with a burr, the first bone portion 71, such as the diaphysis, can be translated medially to increase the first intermetatarsal angle dependent upon the patient's degree of deformity using the surgical guide 1. FIGS. 29A-35 show exemplary steps for performing a preliminary shift, preparing the surgical guide, and then performing the shift to correct the metatarsal angle using the surgical guide 1.

As shown in FIGS. 29A-29C a preliminary shift can be performed following the osteotomy. The draw wire 22 mounted on its support handle 65 is inserted along the osteotomy, as shown in FIG. 29A. When the tip of the draw wire 22 has passed the medial cortex and is in the medullary canal of the first bone portion 71 (e.g., the diaphysis of the metatarsal), the support handle 65 is rotated to position the draw wire 22 in the longitudinal axis of the metatarsal 70 and then laterally shift the second bone portion 72 (e.g., the head of the metatarsal), as shown in FIGS. 29B-29C.

The surgical guide can be prepared for use by retracting the aiming piece 9 into a proximal position inside the second slide 10 of the base 4, and retracting the trigger 5 into a proximal position inside the first slide 6 of the head 3, as shown in FIGS. 30A-30D. Then, as shown in FIG. 31A, the joint capsule is incised at the level of the osteotomy towards the second bone portion 72, e.g., the metatarsal head, and the blade 8 (e.g., distal portion 8*ck*) is inserted through the incision. Thereafter, as shown in FIG. 31B, the blade 8 is slid between the joint capsule and the second bone portion 72 such that the blade 8 abuts against the medial edge of the second bone portion 72. This can be performed by rotating the surgical guide 1 about 45 to 90°, as shown in FIGS. 31A-31B.

The surgical guide 1 can be positioned adjacent to the first bone 70. For example, the surgical guide can be positioned such that the blade 8 is in contact with the cut surface of the first bone 70. In particular, a distal portion 8*c* of the blade 8 can contact the second bone portion 72 and a base 8*a* of the blade 8 can contact a cut surface of the first bone portion 71. As an example, FIG. 32A shows positioning and/or orienting the surgical guide 1 relative to the metatarsal 70. In particular, after rotating the surgical guide 1, the base (e.g., proximal portion 8*a*) of the blade 8 is placed in contact with the cut surface of the first metatarsal (first bone) 70, and can be preferably positioned to be as perpendicular as possible to the second metatarsal 75 (second bone adjacent to the first bone). At the same time, the surgical guide 1 can be oriented as parallel as possible to the back of the first metatarsal 70, as shown in FIG. 32B.

Once the surgical guide 1 is appropriately positioned, the trigger 5 can be advanced against the distal portion 8*c* of the blade 8, for example, using the knob 28. Then, a draw wire 22 can be inserted through the incision to retrieve the medullary shaft of the first bone portion 71, as shown in FIG. 33A. The draw wire 22 is inserted through the surgical guide 1, for example, through the hole 8*b* in the blade 8. Once the draw wire 22 is in the medullary shaft of the first bone portion 71, the draw wire assembly can be rotated or tilted with respect to the surgical guide 1 to accommodate the wire 22 in the pivot slot 67 of the trigger 5, as shown in FIG. 33B. The draw wire handle 65 can be screwed to the element 63 or through hole 7 of the trigger 5 to secure the assembly, but the disclosure is not limited to this. The draw wire 22 or the draw wire handle 65 can be secured to the surgical guide 1 by any suitable means, such as but not limited to flanges, clips, clamps, snap-fit connections, and the like. The guide 1 and draw wire handle 65 should be parallel to the back of the first bone 70 (e.g., first metatarsal), as shown in FIG. 33C, and the surgical handle 65 can be used to oriented the first 70 and second 75 bones, as discussed below with respect to FIGS. 34A and 34B.

In the surgical guide 1 shown in FIGS. 33A-33C, the sleeve forming the through hole 7 in the trigger 5 includes the pivot slot 67 extending in a direction substantially parallel to the through hole 7 so as to enable easy insertion of the draw wire 22. Alternatively, the draw wire 22 may be inserted directly into the through hole 7 and then into the medullary shaft instead of being rotated into the through hole 7 via the pivot slot 67 after being inserted into the medullary shaft.

Once the draw wire 22 is secured in place and the draw wire handle 65 is secured to the trigger 5, the handle 65 can be used to manage the orientation of the proximal phalanx and the height of the metatarsal head 72, as shown in FIGS. 34A and 34B. Then, the trigger 5 can be retracted by turning the knob 28 or other means to make the desired shift, i.e., such that the first bone portion 71 is moved relative to the second bone portion 72. In particular, when the trigger 5 is retracted, the first bone portion 71 is drawn (e.g., pulled) by the draw wire 22 in the medial direction while the second bone portion 72 is held by the blade 8 (e.g., by abutting against the distal portion 8*c* of the blade 8) such that the first bone portion 71 is shifted relative to the second bone portion 72 to reduce the metatarsus varus and correct the DMAA, as shown in FIG. 34B.

After making the appropriate shift, the aiming piece 9 is deployed from the base 4, as shown in FIG. 35. In particular, the aiming piece 9 can slide in the proximal direction through the second slide 10 in the base 4 until it contacts skin. Then, the aiming piece 9 can be locked into place. Using the handle, the orientation of the proximal phalanx and the height of the metatarsal head can be adjusted as needed.

Once the orientation has been properly managed, the wires can be placed, as shown in FIGS. 36A-36B. The barrel 20 for aiming the first wire 23, which is the distal (e.g., medial) screw wire, is inserted into the first (distal) cylindrical sleeve 19 of the supporting means 11. The orientation of the distal phalanges and the height of the metatarsal head (second bone portion) 72 is checked. Then, an incision is made at a point where the barrel 20 touches the skin, and the first wire 23 (distal wire) is inserted through the first bone portion 71 and into the second bone portion 72 to fix the first and second bone portions 71, 72 together, as shown in FIG. 30A. As shown in FIG. 36A, the first wire 23 is inserted into the first bone portion 71 and the second bone portion 72 in a direction transverse to an insertion direction of the draw wire 22 into the first bone portion. The first wire 23 is inserted in a state in which the surgical guide 1 together with the draw wire 22 holds relative positions of the first bone portion 71 and the second bone portion 72.

Without releasing the position of the toe, the barrel 20 for aiming the second wire 25, which is the proximal (e.g., lateral) screw wire is inserted into the second (proximal) cylindrical sleeve 19 of the supporting means 11. Then, the second wire 25 is inserted through the first bone portion 71 and into the second bone portion 72 in a similar manner as the first wire 23, as shown in FIG. 36B. The second wire 25 is inserted on a proximal (lateral) side of the first wire 23 so as to extend substantially parallel to the first wire 23. Like the first wire 23, the second wire 25 is inserted in a direction transverse to the insertion direction of the draw wire 22 and is inserted in a state in which the surgical guide 1 together with the draw wire 22 holds relative positions of the first bone portion 71 and the second bone portion 72. Although the figures show inserting the distal wire first and then the proximal wire, this order is not required and may reversed.

Once both wires 23, 25 have been inserted to fix the first and second bone portions 71, 72 (e.g., the diaphysis and metatarsal head), the barrels 20 can be removed from the cylindrical sleeves 19 of the supporting means 11, as shown in FIG. 37A. The aiming piece 9 can then be unlocked and retracted back through the second slide 10 into the base 4, as shown in FIG. 37B. The longitudinal slot 21 in the supporting means 11 permits easy separation of the supporting means 11 from the wires 23, 25, which pass through the slot 21 as the aiming piece 9 retracts back into the base 4. The draw wire assembly can be removed by removing draw wire 22 from the medullary shaft of the first bone portion 71 and the surgical guide 1, and then the surgical guide 1 can be removed, as shown in FIG. 37C. After the surgical guide 1 is removed, screws can be placed over the first and second wires 23, 25 for final fixation of the first and second bone portions 71, 72.

Although the method has been described for fixing the metatarsal head 72 and the diaphysis 71, the method and surgical guide disclosed herein may be used to fix any bone portions together.

Finally, it is quite obvious that the examples that have just been provided are only particular illustrations that are not restrictive with regards to the fields of application of the invention.

The invention claimed is:

1. A reusable surgical guide for insertion of at least one positioning wire into bone portions in osteosynthesis surgery, the reusable surgical guide comprising:

a grip comprising a head and a base, wherein the head extends at one end of the base, a blade secured to the head and extending from the head, the blade having a distal portion adapted to bear on an epiphysis of a metatarsus, a slideable member configured to cooperate with a first slide formed in the head of the grip so as to be displaced relative to the grip along the blade, the slideable member comprising a through hole configured for insertion of a pull wire into a first bone portion in an insertion direction, and an aiming piece configured to cooperate with a second slide formed in the base of the grip so as to be displaced relative to the grip, said aiming piece comprising at a distal end thereof at least one cylindrical sleeve for supporting insertion of at least one positioning wire into the first bone portion and a second bone portion in a direction transverse to the insertion direction, wherein the surgical guide is configured to be extracted while leaving the at least one positioning wire inserted into the first bone portion and the second bone portion.

2. The surgical guide according to claim 1, wherein the base has a circular-arc shape with a concavity directed towards a distal end of the head of said grip.

3. The surgical guide according to claim 1, further comprising a holding assembly for holding a position of the aiming piece, the holding assembly comprising:

a blocking element configured to cooperate with the aiming piece so as to block a movement of the aiming piece, and an actuating element configured to displace the blocking element to hold or permit movement of the aiming piece.

4. The surgical guide according to claim 1, wherein the aiming piece has a circular-arc shape.

5. The surgical guide according to claim 3, wherein the aiming piece has an aperture extending substantially from a proximal end up to the distal end of the aiming piece, said aperture enabling passage of screws cooperating with holes of the grip.

6. The surgical guide according to claim 1, wherein the at least one cylindrical sleeve forms a sheath configured to receive a barrel for aiming the at least one positioning wire.

7. The surgical guide according to claim 6, wherein the sheath includes a longitudinal slot.

8. The surgical guide according to claim 6, wherein the sheath comprises first and second substantially parallel cylindrical sheaths, wherein each of the first and second sheaths is adapted to receive a barrel for aiming first and second positioning wires.

9. The surgical guide according to claim 1, wherein said blade comprises a longitudinal aperture.

10. The surgical guide according to claim 1, further comprising a means for pulling the slideable member.

11. The surgical guide according to claim 1, wherein the through hole of the slideable member is configured to enable pivoting of the pull wire in a sagittal plane of the surgical guide.

* * * * *